(12) United States Patent
D'Aloiso et al.

(10) Patent No.: US 10,137,278 B2
(45) Date of Patent: Nov. 27, 2018

(54) CANNULA STABILIZATION DEVICE

(71) Applicants: Brandon D. D'Aloiso, Pittsburgh, PA (US); Timothy M. Maul, Oakmont, PA (US); Olivia Jackson, Columbus, OH (US); Marlee Hartenstein, Hermitage, PA (US); Eric D. Moe, Fargo, ND (US); Martin Haschak, Scotrun, PA (US)

(72) Inventors: Brandon D. D'Aloiso, Pittsburgh, PA (US); Timothy M. Maul, Oakmont, PA (US); Olivia Jackson, Columbus, OH (US); Marlee Hartenstein, Hermitage, PA (US); Eric D. Moe, Fargo, ND (US); Martin Haschak, Scotrun, PA (US)

( * ) Notice: Subject to any disclaimer, the term of this patent is extended or adjusted under 35 U.S.C. 154(b) by 76 days.

(21) Appl. No.: 15/368,124

(22) Filed: Dec. 2, 2016

(65) Prior Publication Data

US 2017/0157364 A1 Jun. 8, 2017

Related U.S. Application Data

(60) Provisional application No. 62/263,090, filed on Dec. 4, 2015.

(51) Int. Cl.
*A61M 25/02* (2006.01)
*A42B 1/24* (2006.01)
*A61M 1/36* (2006.01)

(52) U.S. Cl.
CPC ............... *A61M 25/02* (2013.01); *A42B 1/24* (2013.01); *A61M 1/3659* (2014.02); *A61M 2025/0206* (2013.01); *A61M 2025/028* (2013.01); *A61M 2025/0213* (2013.01)

(58) Field of Classification Search
CPC ................ A61M 25/02; A61M 1/3659; A61M 2025/028; A61M 2025/0206; A61M 2025/0213; A42B 1/24
USPC .......................................... 606/130; 604/345
See application file for complete search history.

(56) References Cited

U.S. PATENT DOCUMENTS

2008/0100061 A1* 5/2008 Sage .................... A61B 5/6864
285/305
2009/0229041 A1* 9/2009 Tufenkjian ............... A42B 1/24
2/414

* cited by examiner

*Primary Examiner* — Amber Stiles
(74) *Attorney, Agent, or Firm* — K&L Gates LLP

(57) ABSTRACT

A cannula stabilization device has two tubing holders located on opposite ends of a bearing platform, a rotational joint fixedly attached to the bearing platform, and a helmet releasably attachable to the rotational joint. The helmet and the bearing platform are independently rotatable around a common rotational axis when the helmet is attached to the rotational joint.

20 Claims, 22 Drawing Sheets

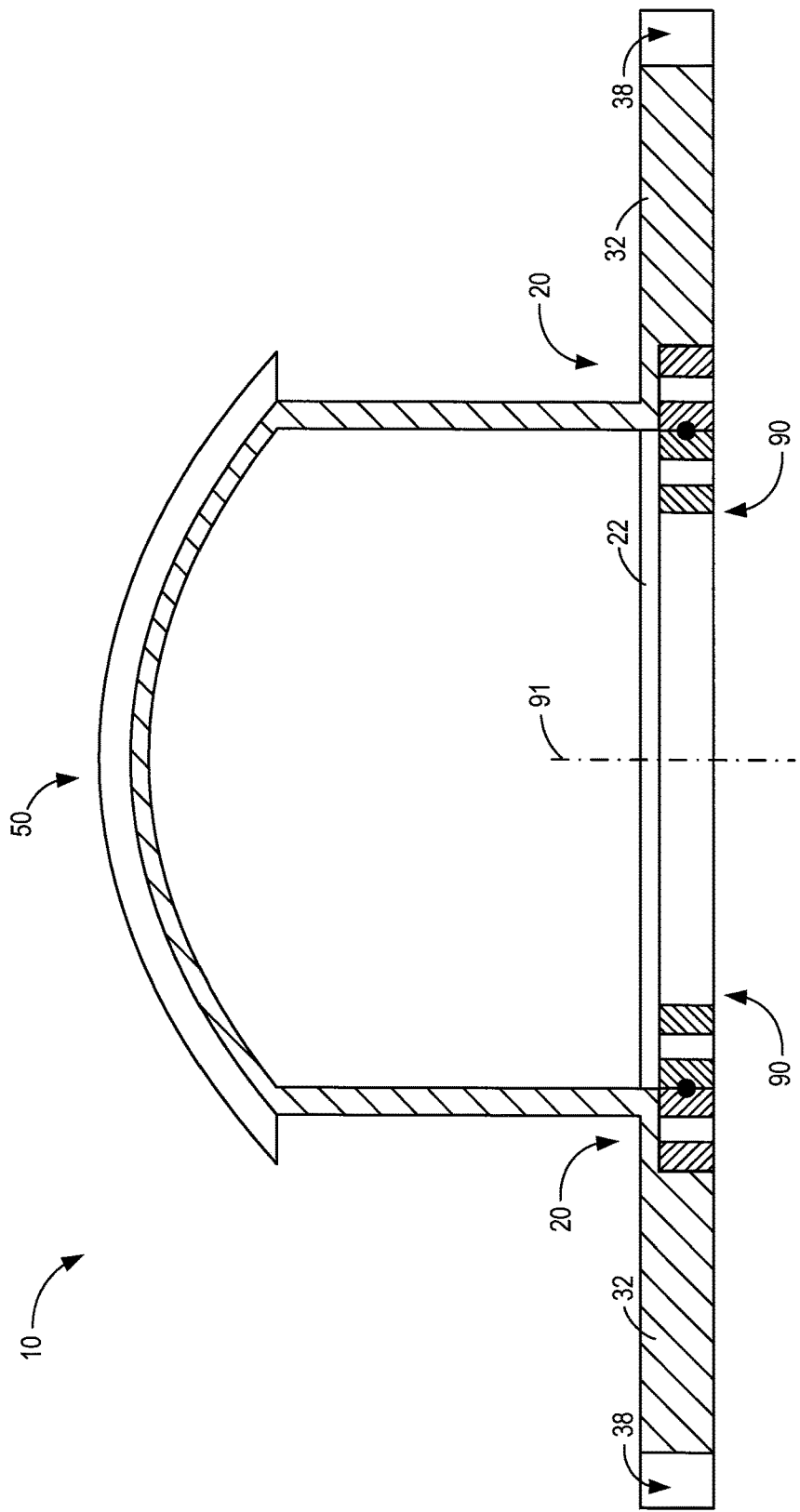

CANNULA STABILIZATION DEVICE

CROSS-REFERENCE TO RELATED APPLICATIONS

This patent application is a non-provisional application filed under 35 U.S.C. § 111(a) and claims priority under 35 U.S.C. § 119(e) to U.S. Provisional Patent Application No. 62/263,090, filed on Dec. 4, 2015. U.S. Provisional Patent Application No. 62/263,090 is incorporated-by-reference into this specification.

BACKGROUND

The information described in this background section is not admitted to be prior art.

Extracorporeal membrane oxygenation (ECMO), also referred to as extracorporeal life support (ECLS), is a clinical life support technique that bypasses the arteriovenous circuit and provides external blood oxygenation to patients suffering from cardiac and/or respiratory failure. For example, ECMO may be used in patients with severe acute respiratory distress syndrome (ARDS) or chronic obstructive pulmonary disease (COPD) as a bridge treatment to lung transplantation. Many patients on ECMO are relatively debilitated and therefore do not possess appreciable ambulatory mobility, which may lead to muscular atrophy and contribute to increased post-transplant morbidity and mortality. As a result, physicians increasingly support the idea that improving a patient's functional status (e.g., their ambulatory mobility) pre-transplant, and while on ECMO, may decrease post-transplant morbidity and mortality. However, pre-transplant rehabilitation of ECMO patients—for example, by walking, i.e., ambulatory ECMO—is difficult to implement in practice because of the size and mass of ECMO equipment (e.g., the blood pump, tubing, oxygenator, heat exchanger, and venous reservoir) and the instability of the ECMO cannulation site.

There are two general types of ECMO techniques: venoarterial (VA ECMO) and veno-venous (VV ECMO). In VA ECMO, a first cannula is surgically or percutaneously inserted through a patient's right jugular vein, right brachiocephalic vein, and superior vena cava, and into their right atrium, and a second cannula is surgically or percutaneously inserted through the patient's right carotid artery and right brachiocephalic artery, and into their aortic arch. In VV ECMO, a double-lumen cannula is surgically or percutaneously inserted through a patient's right jugular vein, right brachiocephalic vein, and superior vena cava, and into their right atrium and inferior vena cava. VV ECMO can also be performed with two separate cannula, for example, a first cannula inserted through a patient's right jugular vein, and a second cannula inserted through a different vein such as the femoral vein. VA ECMO and VV ECMO can also be performed with peripheral cannulation through a patient's femoral vein and femoral artery, or through an axillary approach to the subclavian artery, such as, for example, in the patient's armpit, but peripheral techniques are less common.

In central VA ECMO, deoxygenated blood is withdrawn through the atrial cannula, pumped through an oxygenator and heat exchanger, and the re-oxygenated blood is returned to the patient through the aortic cannula. In VV ECMO, deoxygenated blood is withdrawn from the inferior vena cava and superior vena cava through distal and proximal drainage ports in the dual lumen cannula, pumped through an oxygenator and heat exchanger, and the re-oxygenated blood is returned to the patient through an intermediate infusion port in the dual lumen cannula, which is positioned in the right atrium to direct the re-oxygenated blood flow across the patient's tricuspid valve and into their right ventricle.

The positioning of the cannula in ECMO patients is critical to the success of the technique. Therefore, stabilizing and maintaining the position of the cannula, and the tubing connecting the cannula to the external ECMO circuit, are essential. For example, it is important to not subject the cannula and its insertion site to movements and associated stresses that approach, let alone exceed, the limits of the sutures that hold the cannula in place, which places strict limits on a patient's head and neck movements. The strict limits on ECMO patients' head and neck movements, due to the instability of the cannulation site, make walking while on ECMO (ambulatory ECMO) difficult to perform.

SUMMARY

This specification relates to cannula stabilization devices. More particularly, this specification relates to cannula stabilization devices designed for use with patients having cannulation sites located in their neck and/or upper torso areas.

In one example, a cannula stabilization device comprises a bearing platform, a tubing holder located on a first end of the bearing platform, a tubing holder located on a second end of the bearing platform opposite the first end, and a rotational joint fixedly attached to the bearing platform on a bottom side of the bearing platform. A helmet is releasably attachable to the rotational joint, and the helmet and the bearing platform are independently rotatable around a common rotational axis when the helmet is attached to the rotational joint.

In another example, a cannula stabilization device comprises a bearing platform, a tubing holder located on a first end of the bearing platform, a tubing holder located on a second end of the bearing platform opposite the first end, and a rotational joint fixedly attached to a helmet and releasably attachable to the bearing platform. The helmet and the bearing platform are independently rotatable around a common rotational axis when the rotational joint is attached to the bearing platform.

In another example, a cannula stabilization device comprises a bearing platform, a tubing holder located on a first end of the bearing platform, and a tubing holder located on a second end of the bearing platform opposite the first end. A tubing track is located on a top side of the bearing platform. The tubing track comprises at least two tubing track support members extending from the top side of the bearing platform and connecting to an arcuate shaped tubing support surface. The tubing track further comprises arcuate shaped tubing brackets located on opposite sides of the tubing support surface. A rotational joint is fixedly attached to the bearing platform in a countersunk pocket formed in a bottom side of the bearing platform. The rotational joint comprises an inner ring, an outer ring, and a plurality of ball bearings located between the inner ring and the outer ring. The inner ring and the outer ring are independently rotatable around a common rotational axis. The outer ring of the rotational joint is fixedly attached to the bearing platform, and a helmet is releasably attachable to the inner ring of the rotational joint. The helmet and the bearing platform are independently rotatable around the common rotational axis when the helmet is attached to the rotational joint.

It is understood that the inventions described in this specification are not necessarily limited to the examples summarized in this Summary.

BRIEF DESCRIPTION OF THE DRAWINGS

Various features and characteristics of the inventions described in this specification may be better understood by reference to the accompanying figures, in which:

FIG. 4 is a cross-sectional side view schematic diagram of the cannula stabilization device shown in FIGS. 2A-3F and further comprising the rotational joint shown in FIGS. 3A and 3B positioned in a countersunk pocket located in the bottom side of the bearing platform of the cannula stabilization device;

The reader will appreciate the foregoing features and characteristics, as well as others, upon considering the following detailed description of the inventions according to this specification.

DESCRIPTION

Figure 1A:
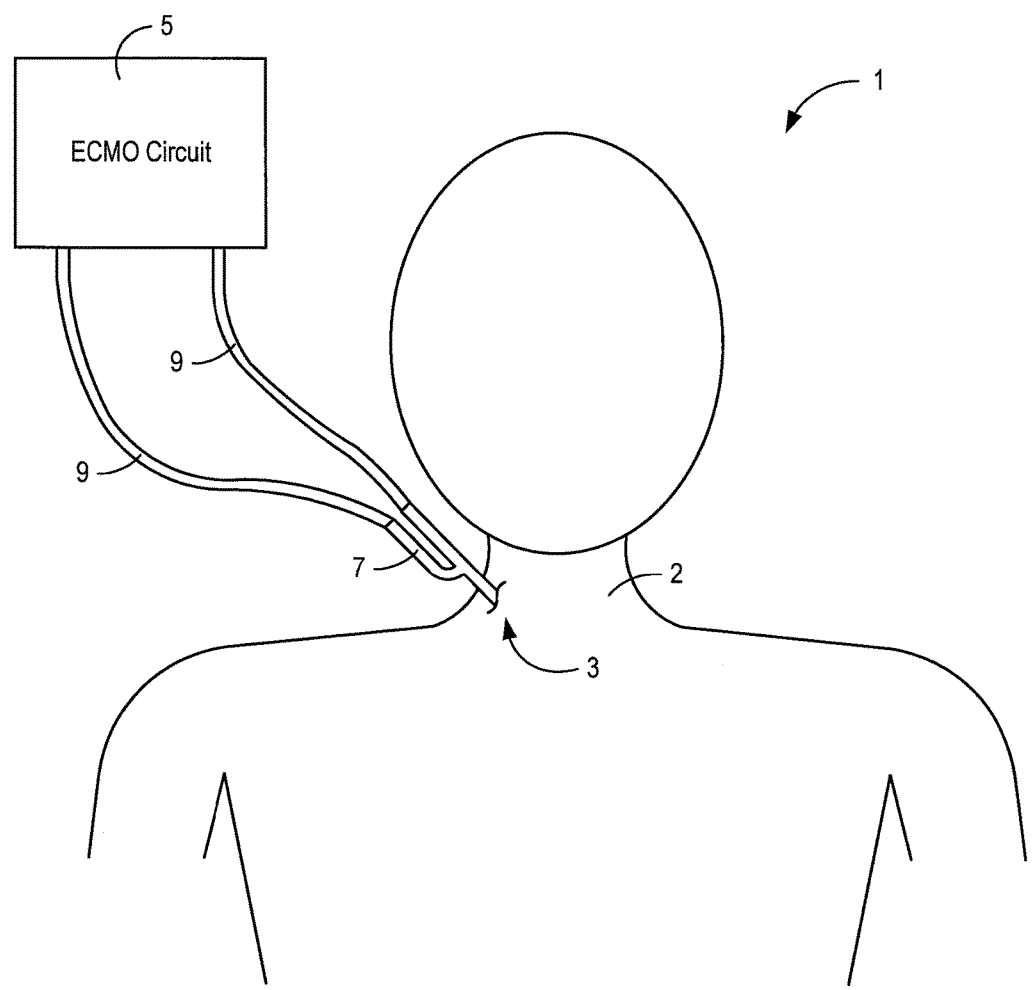
FIG. 1A is a front view schematic diagram of a patient undergoing VV ECMO with a dual lumen cannula inserted through the right jugular vein in the patient's neck.

As described above, the instability of central ECMO cannulation sites in patients' necks limits the ability to perform ambulatory ECMO. Referring to FIG. 1A, an ECMO patient 1 has a cannula 7 inserted through a cannulation site 3 in the patient's neck 2. The cannula 7 is connected to the external ECMO circuit 5 through tubing 9. The cannula 7 and the connected tubing 9 necessarily extend upward from the cannulation site 3 because of the internal positioning of the cannula in the patient's right jugular vein, right brachiocephalic vein, vena cava, and right atrium (or the patient's right carotid artery, right brachiocephalic artery, and aortic arch). The upward orientation of the external portions of the cannula and the attached tubing render the cannulation site relatively unstable and limit a patient's neck movements in the sagittal, coronal, and axial planes.

Figure 1B:
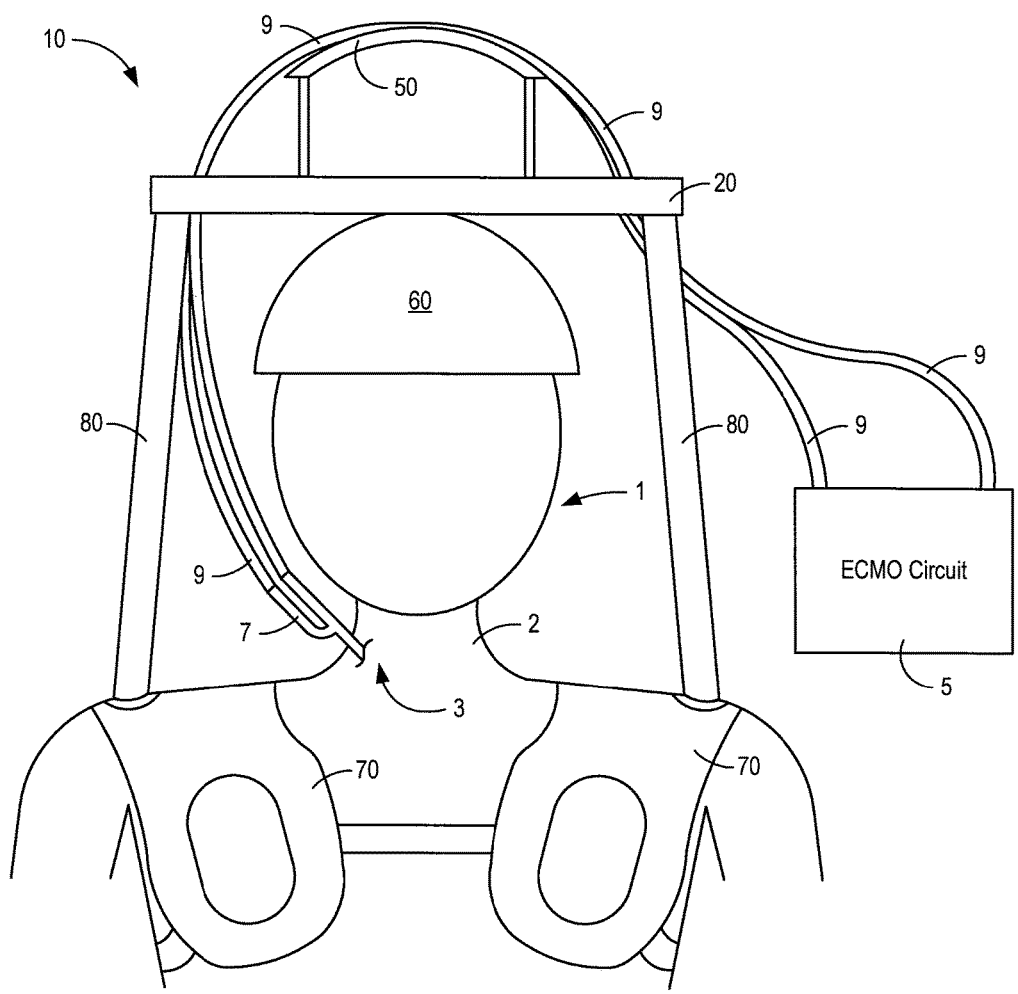
FIG. 1B is a front view schematic diagram of a patient undergoing VV ECMO with a dual lumen cannula inserted through the right jugular vein in the patient's neck and using a cannula stabilization device as described in this specification.
Figure 2A:
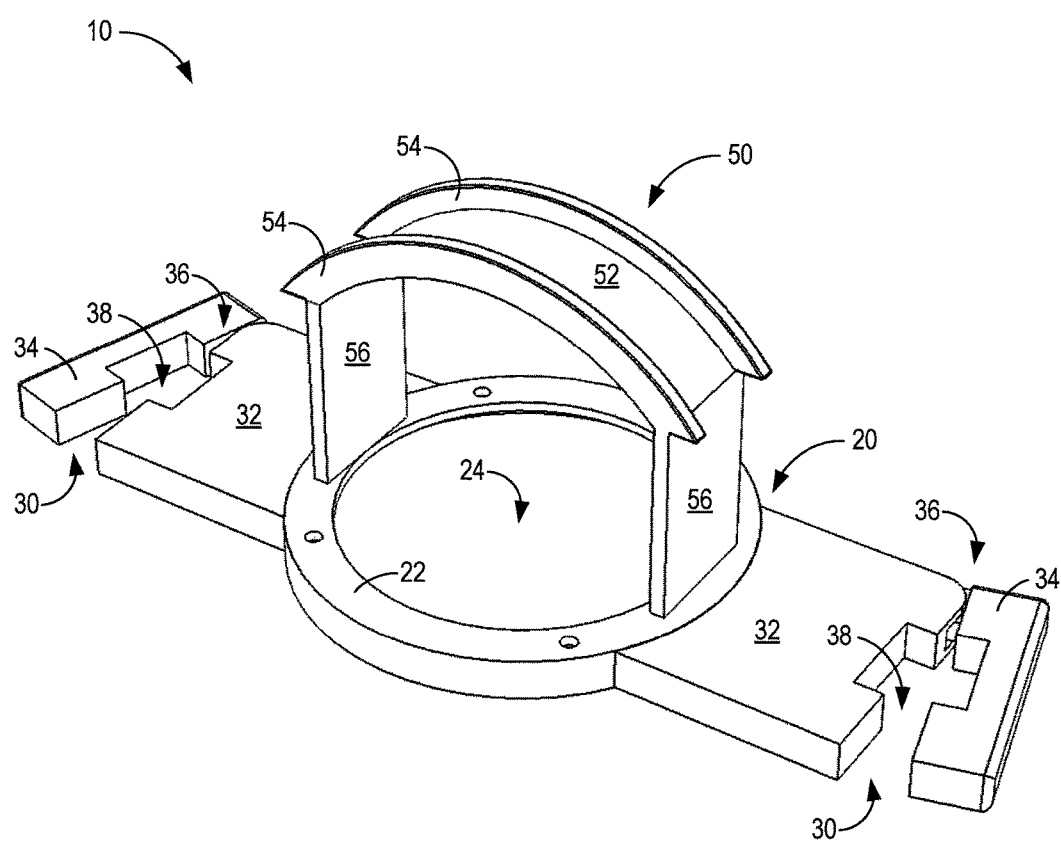
FIGS. 2A, 2B, and 2C are perspective view schematic diagrams of a cannula stabilization device comprising a bearing platform, tubing holders, and a tubing track.
Figure 2B:
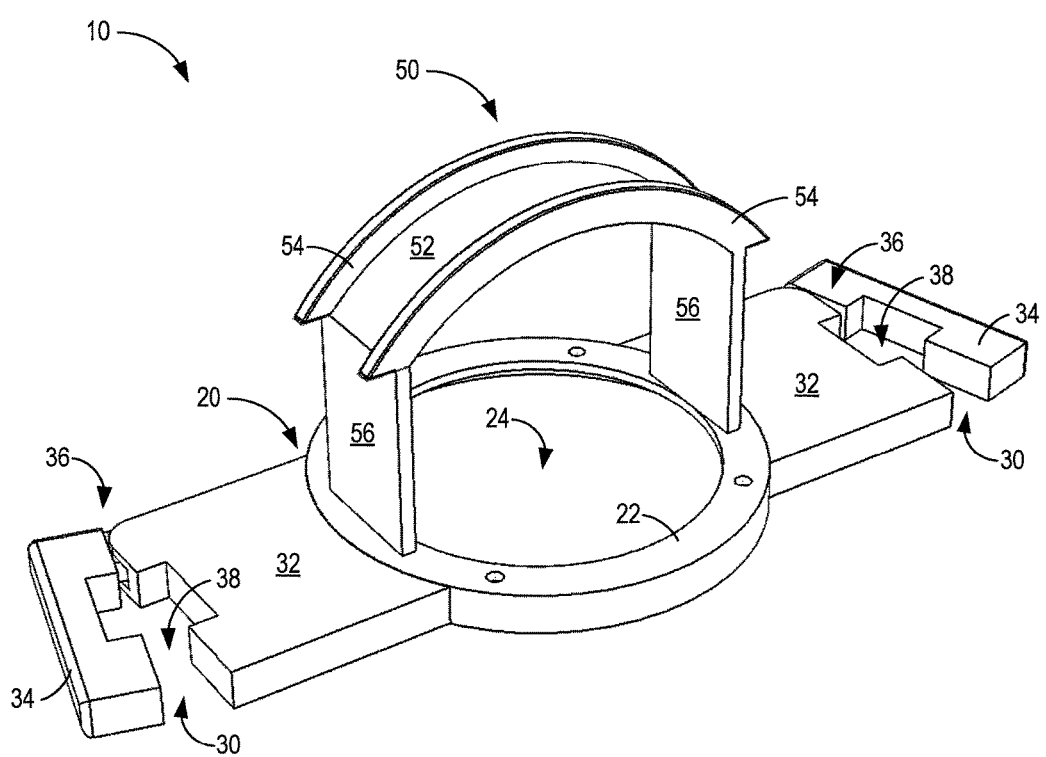
Figure 2C:
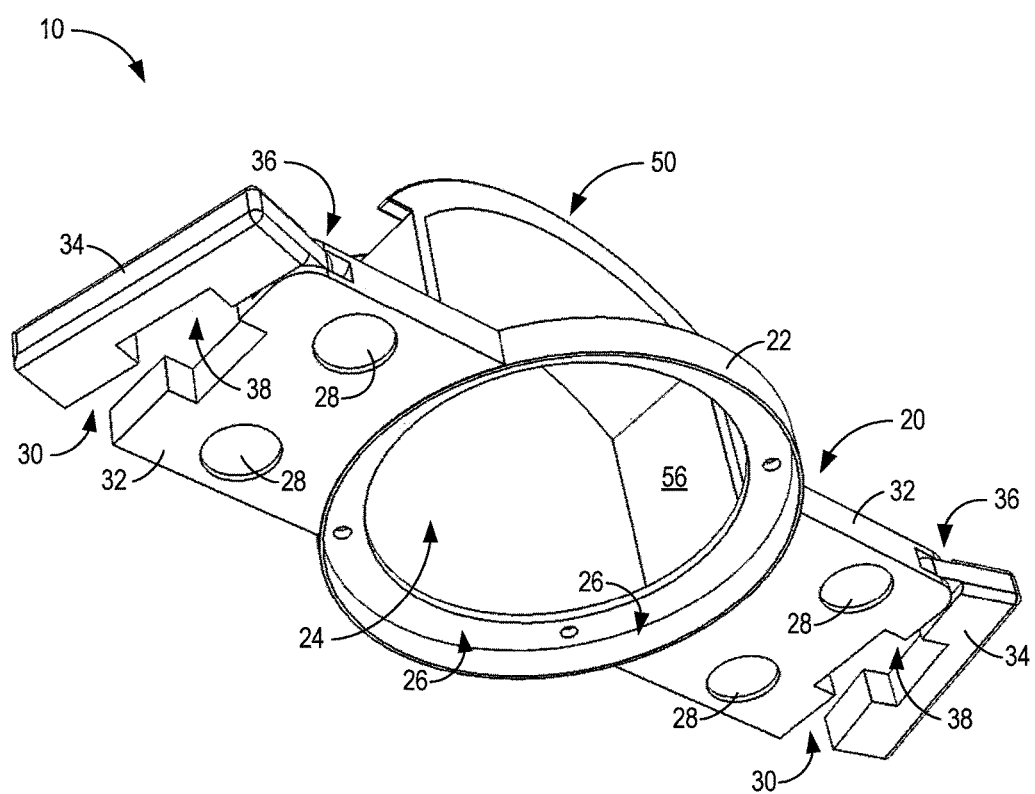
Figure 2D:
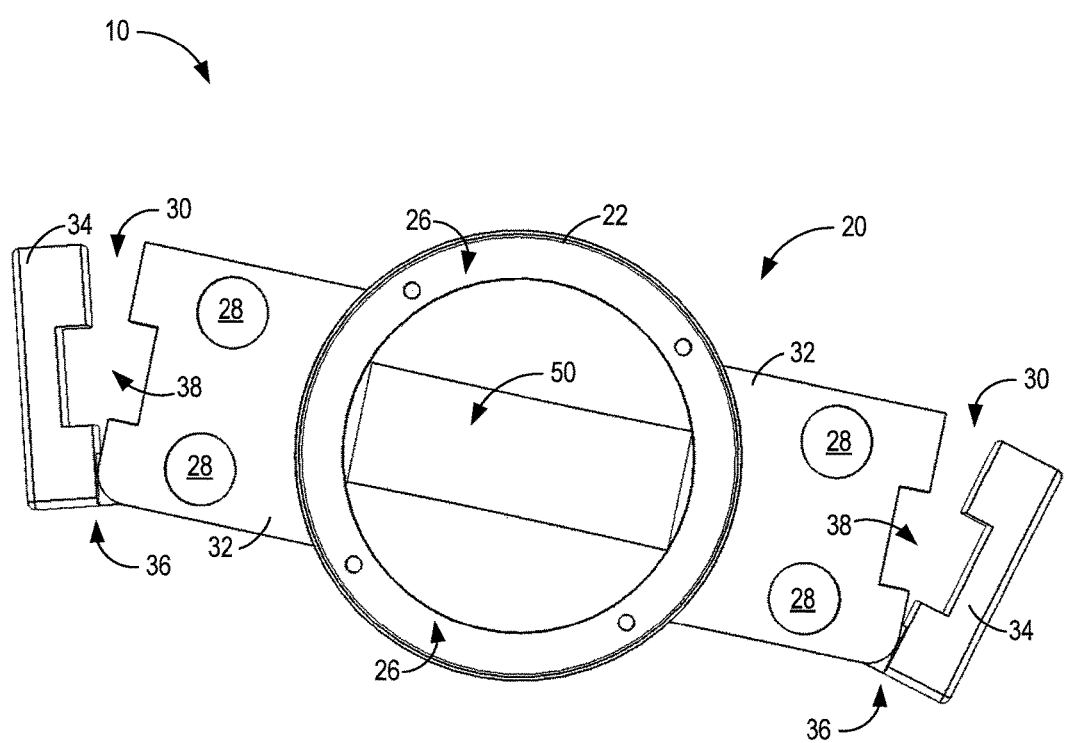
FIG. 2D is a bottom view schematic diagram of the cannula stabilization device shown in FIGS. 2A-2C.
Figure 2E:
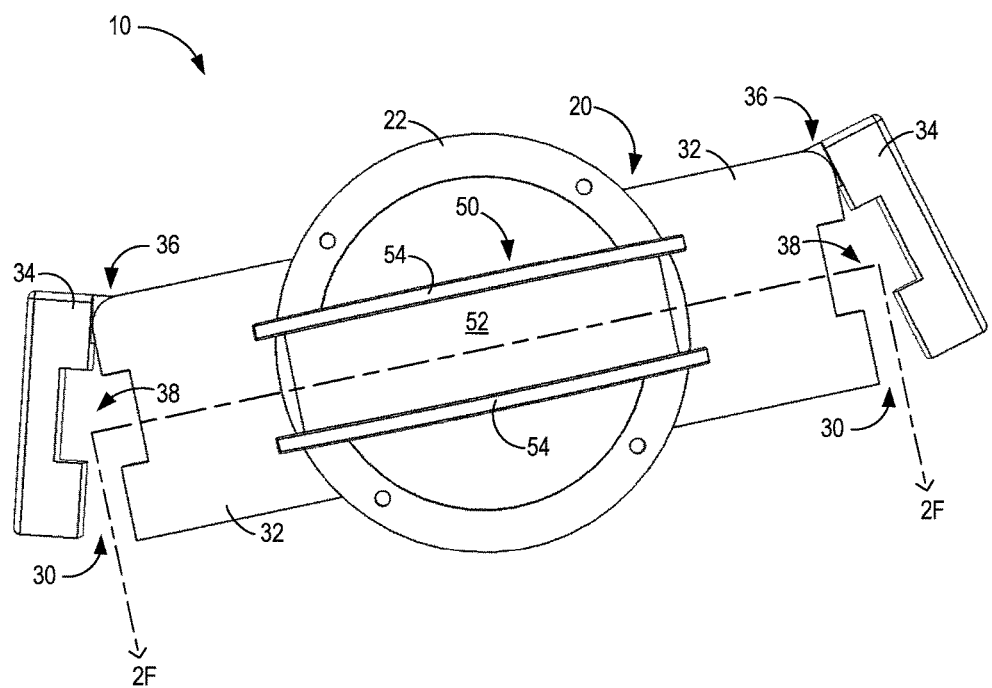
FIG. 2E is a top view schematic diagram of the cannula stabilization device shown in FIGS. 2A-2D.
Figure 2F:
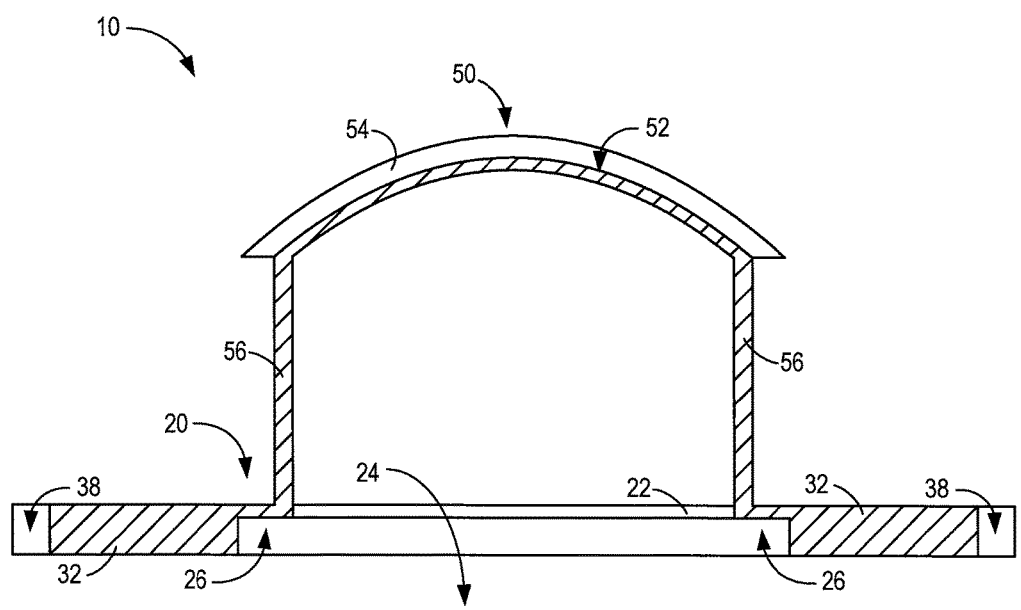
FIG. 2F is a cross-sectional side view schematic diagram of the cannula stabilization device perpendicular to the plane 2F-2F as shown in FIG. 2E.

Referring to FIG. 1B, a cannula stabilization device 10 stabilizes the cannulation site 3 in the patient's neck 2 by passively controlling the patient's neck and head movements and limiting the movements to a degree that does not dislodge the cannula 7 or disrupt the cannulation site 3. The cannula stabilization device 10 allows the patient 1 to safely walk while on ECMO and therefore facilitates ambulatory ECMO. The cannula stabilization device 10 comprises a bearing platform 20, a rotational joint (not shown), a tubing track 50, and a helmet 60. The helmet 60 is releasably attachable to the bearing platform 20 through the rotational joint. The cannula stabilization device 10 comprises tubing holders (not shown) positioned on the opposite ends of the bearing platform 20 and configured to secure and route the tubing 9 from the cannula 7, along the tubing track 50, over the patient's head, and safely to the ECMO circuit 5 (when the patient 1 is wearing the helmet 60 attached to the bearing platform 20). The cannula stabilization device 10 optionally comprises a base garment 70 and bearing platform support members 80. The bearing platform support members 80 are releasably attachable to the bottom side of the bearing platform 20 and to the base garment 70.

In use, the rotational joint provides for rotation of the helmet 60 in the axial/transverse plane (actuated by axial rotation of the patient's head and neck) independent of the attached bearing platform 20. The independent rotation of the helmet 60 relative to the bearing platform 20 effectively decouples movement of the patient's head from movement of the cannula 7 and the tubing 9. The optional attachment of the bearing platform 20 to the base garment 70, when worn by the patient 1, and through the bearing platform support members 80, controls and limits the patient's head and neck movement in the sagittal/median plane (i.e., front-to-back or nodding rotation) and the coronal/frontal plane (i.e., shoulder-to-shoulder rotation).

Referring to FIGS. 2A-2F, cannula stabilization device 10 comprises the bearing platform 20, a first tubing holder 30 located on a first end of the bearing platform 20, and a second tubing holder 30 located on a second end of the bearing platform 20 opposite the first end of the bearing platform 20. The tubing holders 30 each comprise a holder arm 34 attached to a holder base 32 through a hinge 36. The holder arms 34 and the holder bases 32 each comprise gaps that together form tubing apertures 38 through the holders 30 when the holders 30 are in a closed configuration. The tubing apertures 38 extend between the top side and the bottom side of the bearing platform 20. The tubing apertures 38 provide a pathway for routing tubing from an inserted cannula, through the bearing platform 20, along the tubing track 50, over a patient's head, back through the bearing platform 20, and safely to an ECMO circuit. The tubing holders 30 secure the tubing to the bearing platform 20 and maintain the positioning of the tubing along the tubing track 50.

Although not shown in FIGS. 2A-2F, the holder arms 34 and/or the holder bases 32 may further comprise solid foam located in the gaps. For example, solid foam layers may be located on the surfaces of the gaps in the holder arms 34 and/or the holder bases 32, thereby providing a foam lining to the tubing aperture 38 when the tubing holders 30 are in a closed configuration. A solid foam lining in the tubing aperture 38 may cushion and protect the tubing from mechanical abrasion by the holder arms 34 and/or the holder bases 32, may further secure the tubing in the tubing aperture 38 without pinching or kinking the tubing, and allows a single tubing aperture 38 to accommodate tubing of different sizes. The solid foam located in the gaps may comprise, for example, a polyurethane foam material.

Although not shown in FIGS. 2A-2F, the tubing holders 30 may further comprise a closure mechanism to secure the holder arms 34 in a closed configuration. For example, a hook-and-loop closure (i.e., Velcro) strap may be respectively connected to surfaces of the holder arms 34 and the holder bases 32.

Still referring to FIGS. 2A-2F, the tubing track 50 is located on the top side of the bearing platform 20. The tubing track 50 comprises two tubing track support members 56 extending from the top side of the bearing platform and connecting to a tubing support surface 52. The tubing support surface 52 is arcuate shaped. The tubing track 50 further comprises arcuate shaped tubing brackets 54 located on opposite sides of the tubing support surface 52.

A bearing aperture 24 is located in a bearing base 22 of the bearing platform 20. The bearing aperture 24 extends through the bearing platform 20 from the top side of the bearing platform 20 to the bottom side of the bearing platform 20. A countersunk pocket 26 is formed in the bottom side of the bearing platform 20. The countersunk pocket 26 is configured to hold a rotational joint (not shown in FIGS. 2A-2F). The countersunk pocket 26 is located in concentric alignment with the bearing aperture 24.

The bearing platform 20 shown in FIGS. 2A-2F comprises the holder bases 32 and a bearing base 22. The holder bases 32 and the bearing base 22 may comprise separate components that are assembled and connected together to form a portion of the bearing platform 20. Alternatively, the holder bases 32 and the bearing base 22 may comprise integral regions of a single monolithic component comprising the bearing platform 20. Similarly, the tubing track 50 (and its constituent components, described above) and the bearing platform 20 may comprise separate components that are assembled and connected together. Alternatively, the tubing track 50 (and its constituent components, described above) and the bearing platform 20 (or any component of the bearing platform, such as, for example, the bearing base 22) may comprise integral regions of a single monolithic component.

The bearing platform 20, the tubing holders 30, and the tubing track 50 (including any constituent components, described above) may be made of a plastic material of construction such as, for example, polyethylene, polypropylene, polycarbonate, polyamide, or poly(acrylonitrile-butadiene-styrene) (ABS). The bearing platform 20, the tubing holders 30, and the tubing track 50 (including any constituent components, described above) can be produced, for example, by injection molding or three-dimensional printing of a plastic material of construction.

Figure 3A:
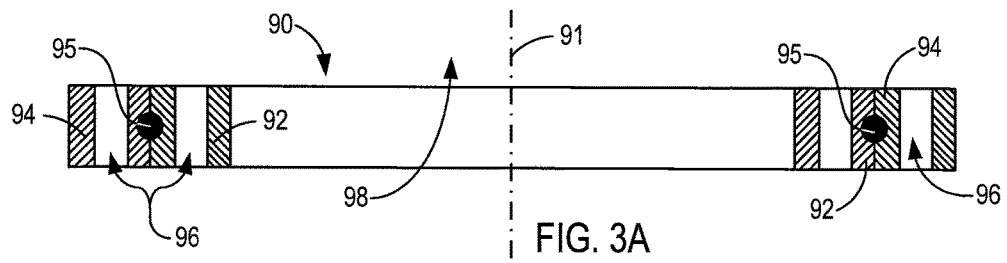
FIG. 3A is a cross-sectional side view schematic diagram of a rotational joint comprising two concentric rings having independent rotational freedom.
Figure 3B:
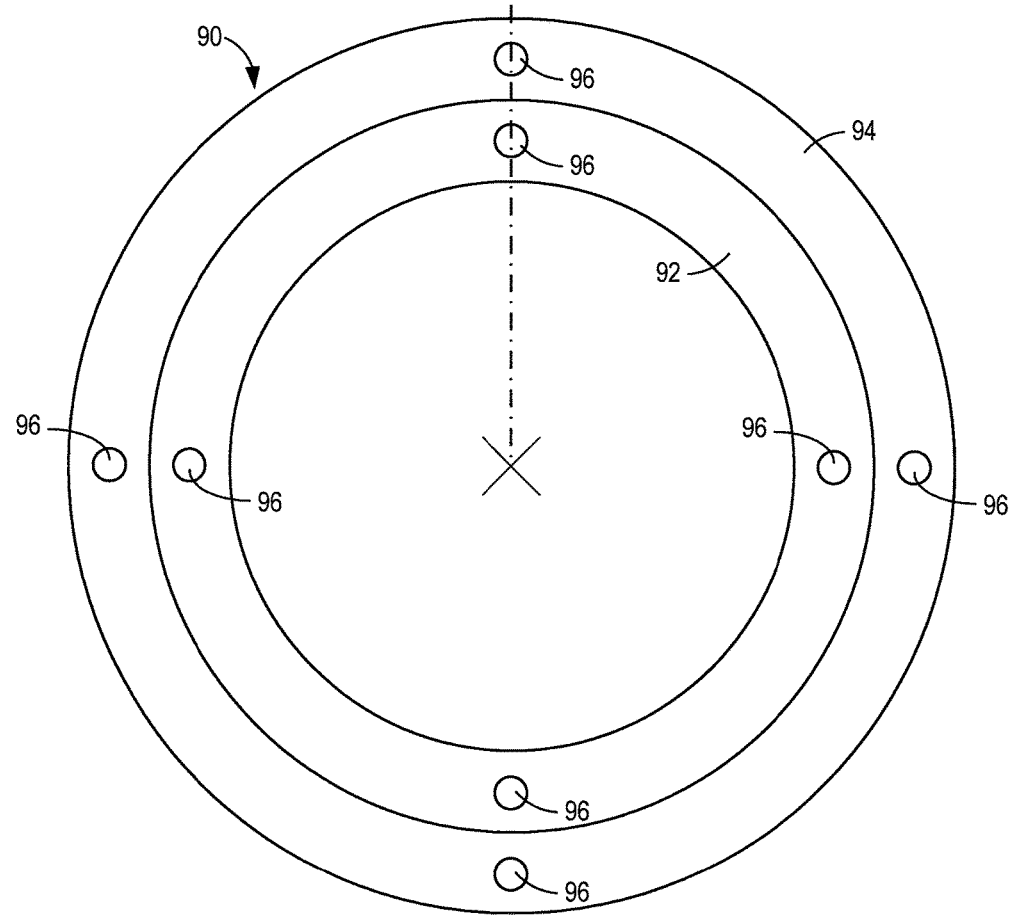
FIG. 3B is a top/bottom view schematic diagram of the rotational joint shown in FIG. 3A.

As described above, the countersunk pocket 26 in the bottom side of the bearing platform 20 is configured to hold a rotational joint. Referring to FIGS. 3A and 3B, a rotational joint 90 comprises an inner ring 92, an outer ring 94, and a plurality of ball bearings 95 located between the inner ring 92 and the outer ring 94. The inner ring 92 and the outer ring 94 are independently rotatable around a common rotational axis 91. The rotational joint 90 comprises a rotational joint aperture 98 surrounded by the inner surface of the inner ring 92 (i.e., the rotational joint 90 is annularly shaped, see FIG. 3B). The inner ring 92 and the outer ring 94 of the rotational joint 90 may comprise fastener holes 96 to facilitate the independent attachment of each ring 92/94 of the rotational joint 90. The rotational joint may comprise a material of construction such as aluminum, for example.

Figure 3C:
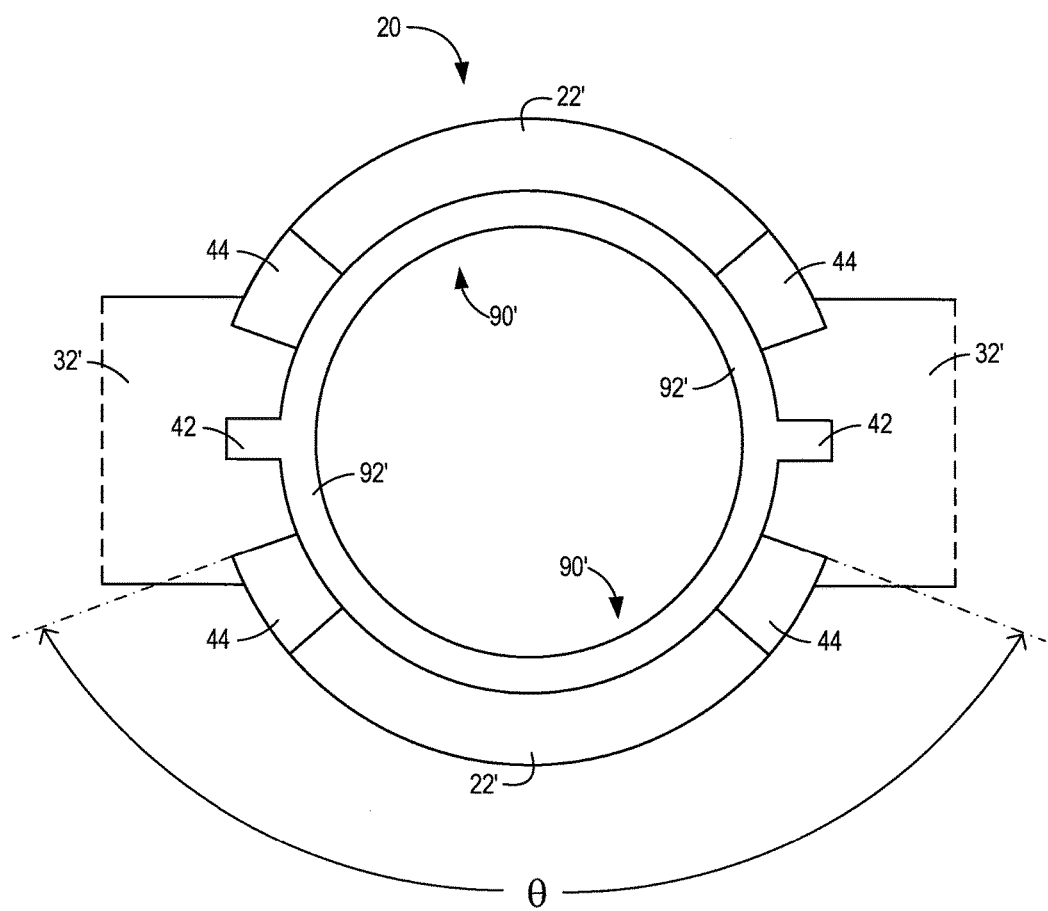
FIG. 3C is a partial top view schematic diagram of a bearing platform comprising a rotational joint positioned therein and rotational stops configured to prevent over-rotation of a patient's head.

Although not shown in FIGS. 3A and 3B, the rotational joint 90 can comprise a rotational stop configured to prevent over-rotation of a patient's head. For example, referring to FIG. 3C, a bearing platform 20' comprises integrally-formed bearing base 22' and holder bases 32'. The bearing platform 20' further comprises rotational stops 44, which may comprise integral projections extending from the top surface of the bearing platform 20'. A rotational joint 90' is fixedly attached to the bearing platform 20' on the bottom side of the bearing platform (as described, for example, below in connection with FIGS. 4 and 5). The rotational joint 90' comprises an inner ring 92' which is independently rotatable relative to the bearing platform 20'. The inner ring 92' comprises rotational stops 42, which may comprise integral projections extending from the top surface of the inner ring 92', or integral projections extending from the top surface of a bearing aperture cap (not shown) attached to the inner ring 92'. The rotational stops 42 of the inner ring 92' are located in an overlapping plane with the rotational stops 44 of the bearing platform 20'. Therefore, when a patient rotates their head and neck, as described in greater detail below, the patient's rotational range is limited to the angle θ defined by the opposite positions at which the rotational stops 42 mechanically contact the rotational stops 44.

As shown in FIG. 4, the rotational joint 90 is fixedly attached to the bearing platform 20 on the bottom side of the bearing platform. The rotational joint 90 is fixedly attached to the bearing platform 20 in the countersunk pocket 26 formed in the bottom side of the bearing platform. The rotational joint 90 is located in concentric alignment with the bearing aperture 24 through the bearing platform 20. The outer ring 94 of the rotational joint 90 is fixedly attached to the bearing platform 20, but the inner ring 92 of the rotational joint 90 is not attached to the bearing platform 20. Therefore, the inner ring 92 of the rotational joint 90 is independently rotatable around the rotational axis 91 relative to the bearing platform 20 (and the tubing holders 30 and tubing track 50).

The rotational joint 90 can be fixedly attached to the bearing platform 20 using, for example, fasteners (e.g., screws, bolts, or the like) positioned through the fastener holes 96 in the outer ring 94 of the rotational joint 90. The rotational joint 90 can be fixedly attached to the bearing platform 20 using, for example, an adhesive applied to the outer surface of the outer ring 94 of the rotational joint 90 and/or the surfaces of the countersunk pocket 26 formed in the bottom side of the bearing platform 20. The rotational joint 90 can be fixedly attached to the bearing platform 20 using, for example, an interference fitting (i.e., a press fitting or friction fitting) between the outer surface of the outer ring 94 of the rotational joint 90 and the surfaces of the countersunk pocket 26 formed in the bottom side of the bearing platform 20.

Figure 5:
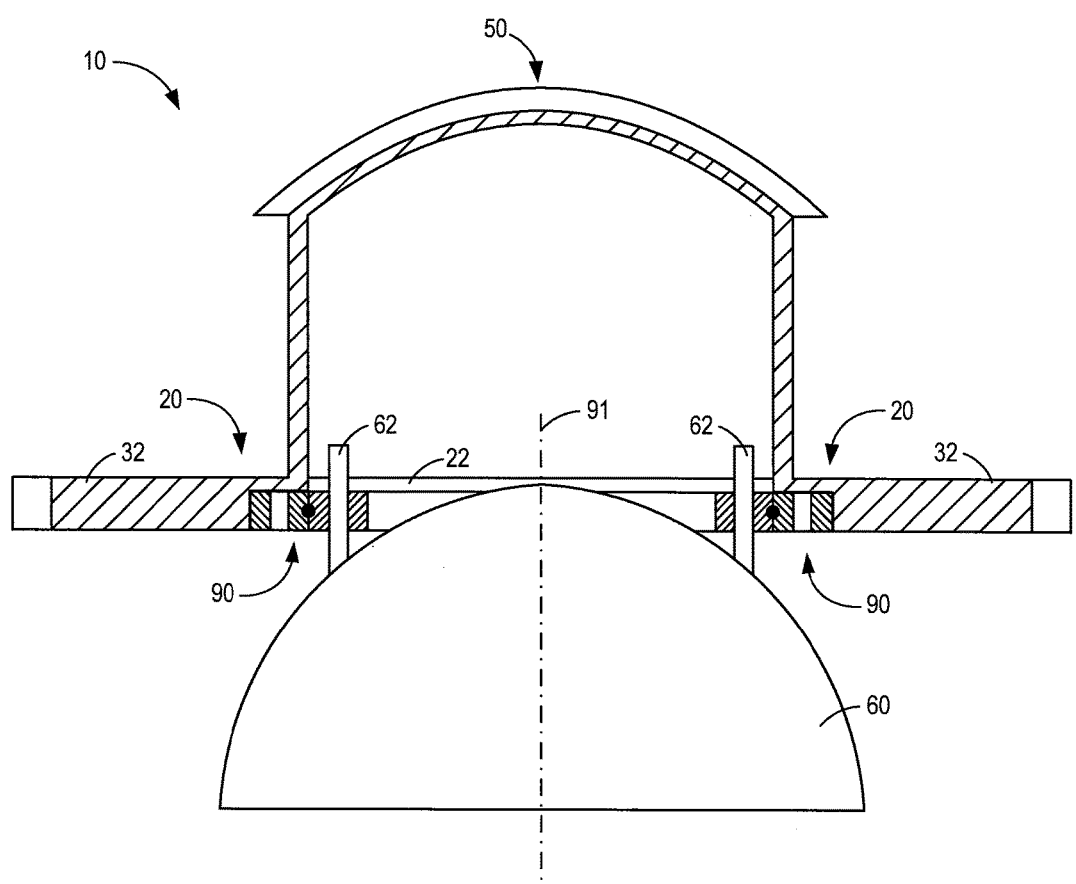
FIG. 5 is a cross-sectional side view schematic diagram of the cannula stabilization device shown in FIG. 4 attached to a patient helmet with fasteners.
Figure 9:
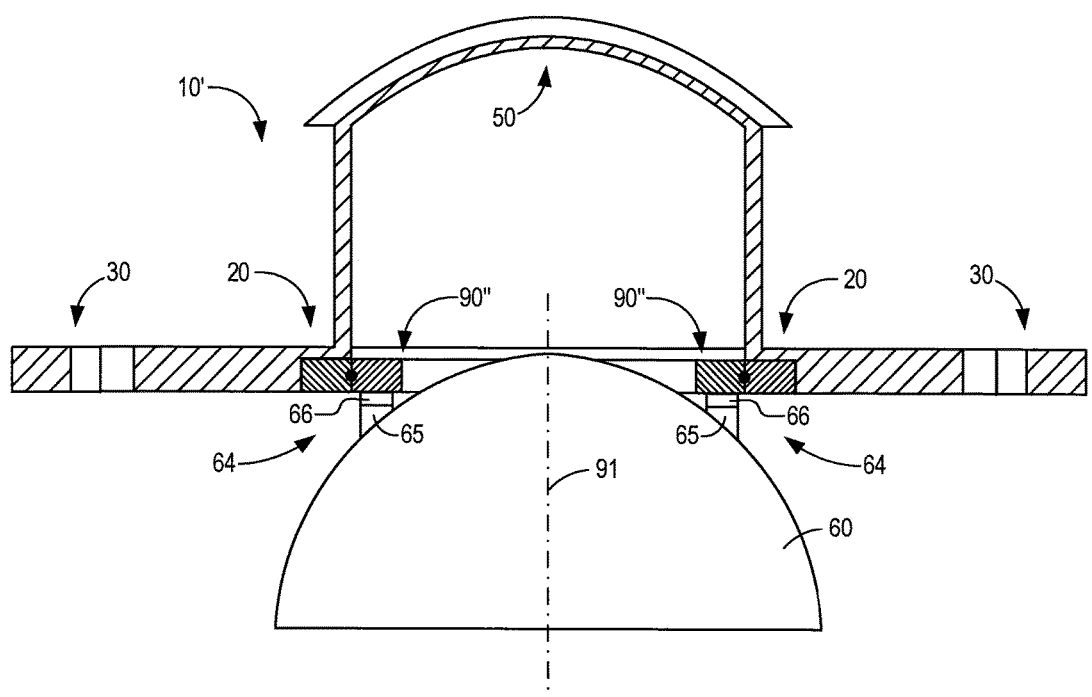
FIG. 9 is cross-sectional side view schematic diagram of a cannula stabilization device attached to a patient helmet with magnetic attachments.

As shown in FIG. 5, the helmet 60 is releasably attachable to the rotational joint 90. The helmet 60 is releasably attachable to the inner ring 92 of the rotational joint 90. Therefore, when the helmet is attached to the rotational joint 90 through the inner ring 92, the helmet 60 and the bearing platform are independently rotatable around the common rotational axis 91. The helmet 60 is releasably attachable to the inner ring 92 of the rotational joint 90 using, for example, fasteners 62 (e.g., screws, bolts, pins, or the like) that are fixedly attached to the helmet 60 and positioned through the fastener holes 96 in the inner ring 92 of the rotational joint 90. Alternatively, the helmet 60 is magnetically (releasably) attachable to the inner ring 92 of the rotational joint 90 (see FIG. 9, described in detail below). Alternatively, the inner ring 92 may be attached to a piece of material (not show) that extends within the circumference of the inner ring 92, providing a cap over the rotational joint aperture 98 and the bearing aperture 24, and the helmet is releasably attachable to the inner ring 92 through the bearing aperture cap using, for example, one or more fasteners (e.g., screws, bolts, pins, or the like) or magnetic attachments.

Figure 6A:
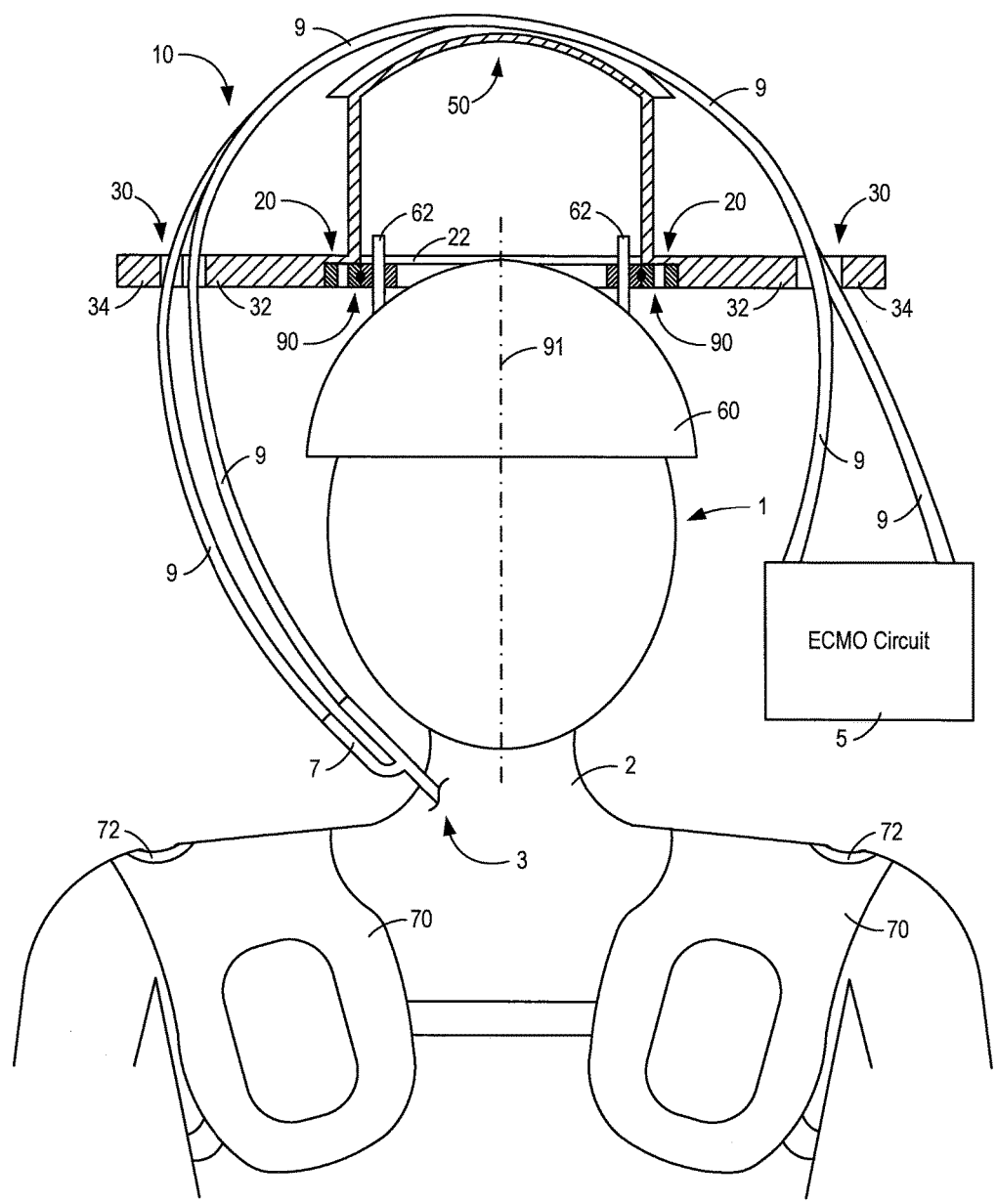
FIGS. 6A and 6B are front view schematic diagrams of a patient undergoing VV ECMO with a dual lumen cannula inserted through the right jugular vein in the patient's neck and using a cannula stabilization device as shown in FIG. 5.
Figure 6B:
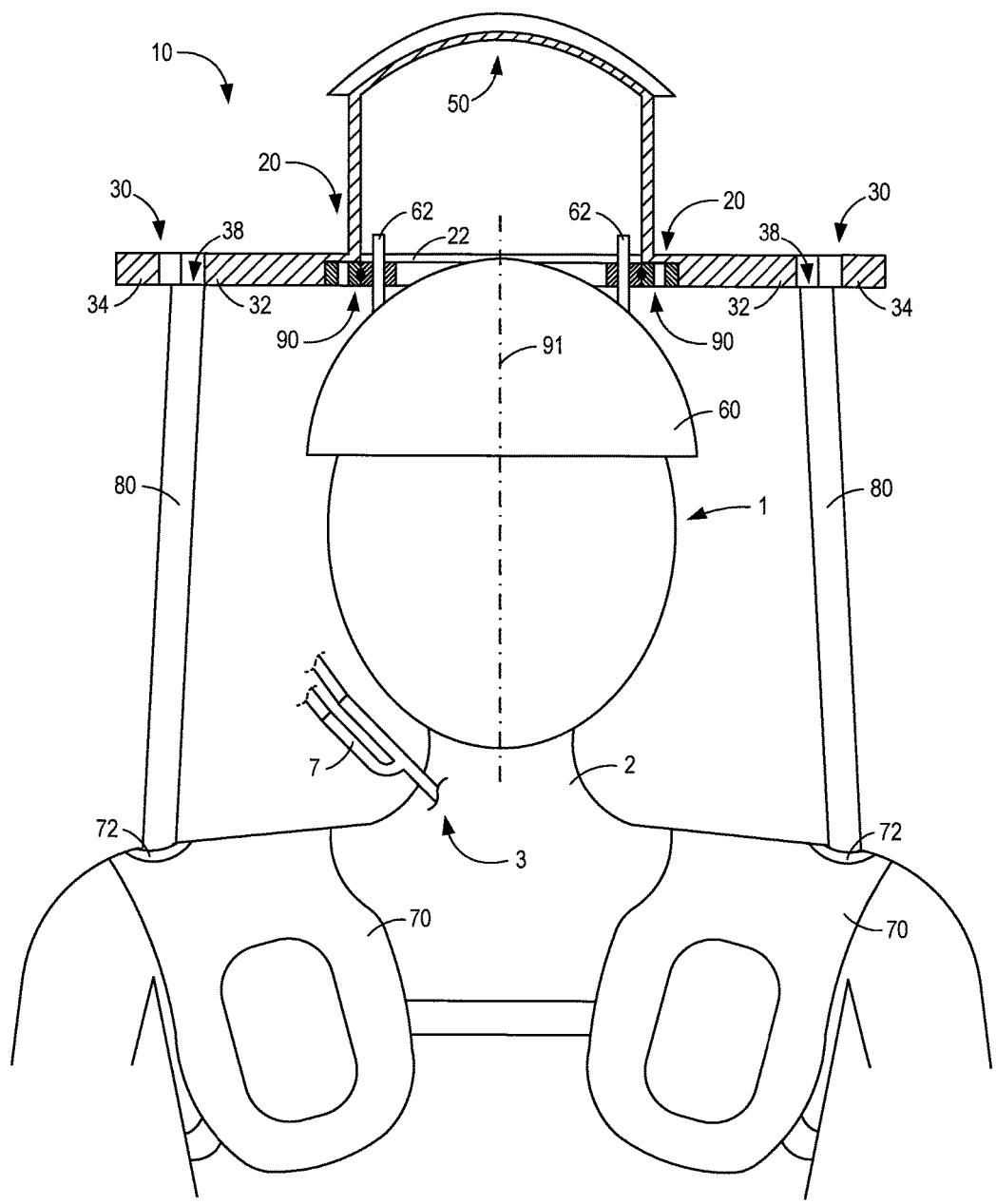

Referring to FIGS. 6A and 6B, the cannula stabilization device 10 stabilizes the cannulation site 3 in the patient's neck 2 by passively controlling the patient's neck and head movements and limiting the movements to a degree that does not dislodge the cannula 7 or disrupt the cannulation site 3. For sake of clarity, the optional bearing platform support members 80 are omitted from FIG. 6A and the tubing and ECMO circuit are omitted from FIG. 6B. The rotational joint 90 between the helmet 60 and the bearing platform 20, the tubing holders 30, and the tubing track 50 may allow the patient 1 to rotate their head in the axial/transverse plane, for example, up to a total of 40 degrees (e.g., ±20 degrees relative to the sagittal/median plane) without appreciably moving the tubing 9 secured and routed by the bearing platform 20, the tubing holders 30, and the tubing track 50. The independent rotation of the helmet 60 and the patients head in the axial/transverse plane relative to the bearing platform 20 effectively decouples the axial movement of the patient's head from movement of the cannula 7 and the tubing 9.

The rotational joint 90 only allows independent rotation of the helmet 60 and the bearing platform 20 (and the tubing holders 30 and the tubing track 50) in the axial/transverse plane around rotational axis 91. The helmet 60, the bearing platform 20, the tubing holders 30 and tubing track 50 are not independently moveable, rotationally or translationally, in any other direction or plane, when the helmet is attached to the rotational joint 90. In embodiments comprising the optional base garment 70 and bearing platform support members 80, the attachment of the bearing platform 20 to the base garment 70 through the bearing platform support members 80, prevents the bearing platform 20, the tubing holders 30, and the tubing track 50 from moving rotationally or translationally relative to the patient's shoulders and upper torso. This controls and limits the patient's head and neck movement in the sagittal/median plane (i.e., front-to-back or nodding rotation) and in the coronal/frontal plane (i.e., shoulder-to-shoulder rotation).

The degree of head and neck movement in the sagittal/median plane and in the coronal/frontal plane can be controlled by the relative tightness of the fit of the helmet on the patient's head (using, for example, chin straps, head straps, and the like, not shown). To ensure effective stabilization of the cannula insertion site 3, the helmet 60 should be fitted on the patient 1 so that the patient's head does not rotate in the sagittal/median plane more than ±10 degrees relative to the coronal/frontal plane, and so that the patient's head does not rotate in the coronal/frontal plane more than ±10 degrees relative to the sagittal/median plane.

The limits on the head and neck rotation of a patient using the cannula stabilization device will ensure that a cannula does not displace from a cannula insertion site more than 1 inch (2.45 cm) while walking or otherwise moving, which facilitates ambulatory ECMO by minimizing the potential for insertion site injury, bleeding, cannula migration, and intravascular damage.

The base garment 70 may comprise any suitable garment configured to be worn by a cannulated patient. The base garment 70 must fit over a patient's shoulders and be securable around the patient's upper torso. For example, the base garment 70 may comprise adjustable shoulder pads or a vest. The cannula stabilization device 10 may comprise at least two (e.g., four) bearing platform support members 80, which are releasably attachable to the bottom side of the bearing platform 20 and to the base garment 70. The bearing platform support members 80 may comprise length-adjustable telescoping rods. The bearing platform support members 80 may be magnetically attachable to the base garment 70. The bearing platform support members 80 may be magnetically attachable to the bottom side of the bearing platform 20.

Figure 7:
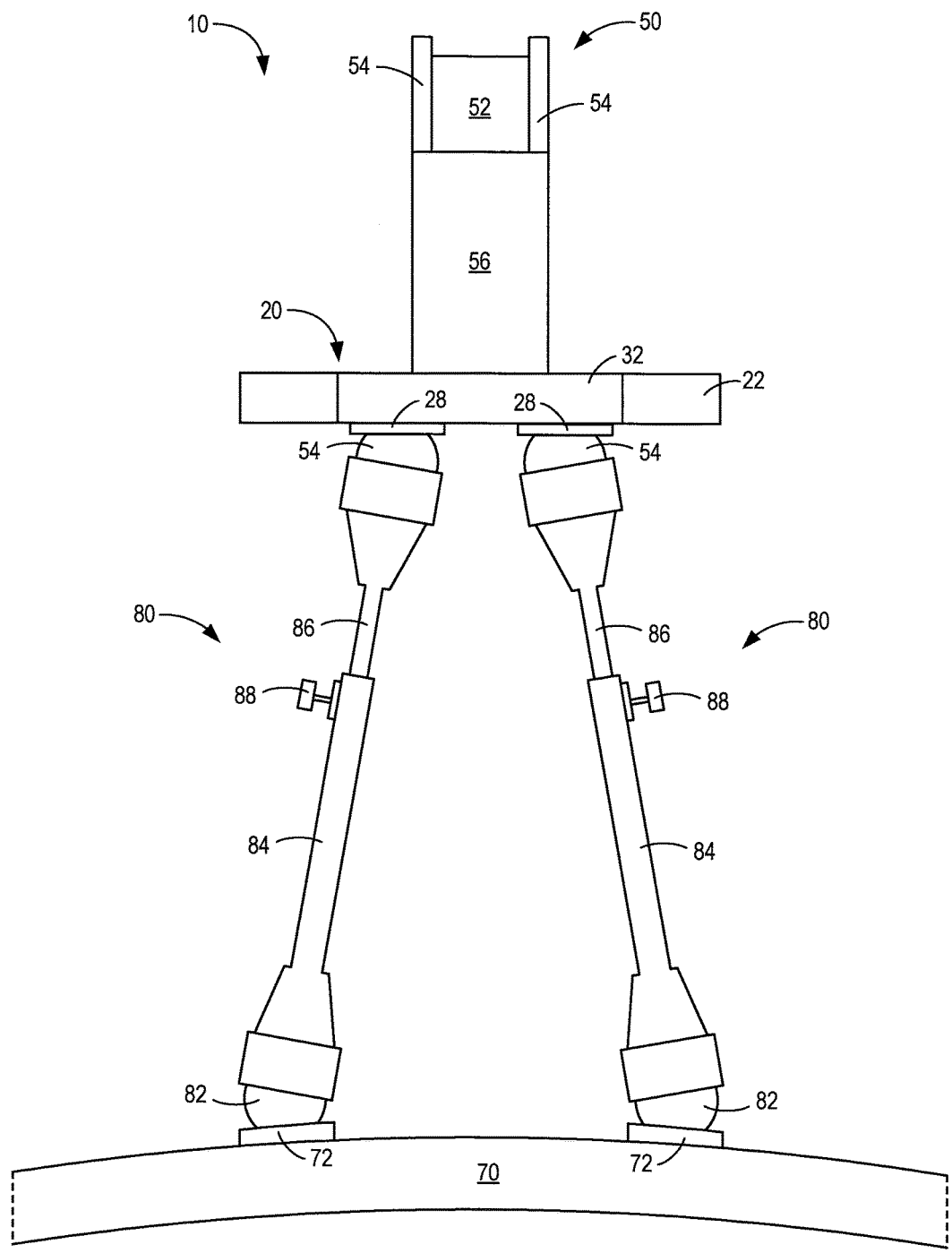
FIG. 7 is a side view schematic diagram of a cannula stabilization device showing the bearing platform attached to platform support members attached to a base garment.
Figure 8A:
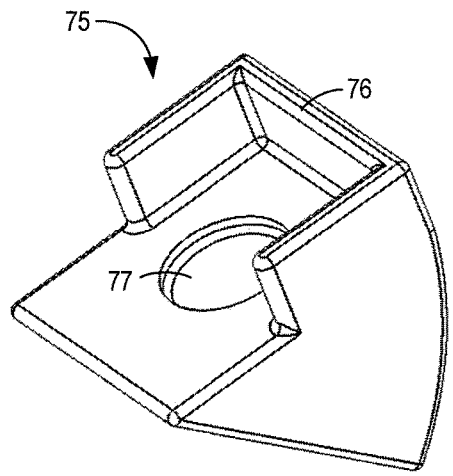
FIGS. 8A-8D are perspective view schematic diagrams of adjustable base garment attachments configured to engage platform support members.
Figure 8B:
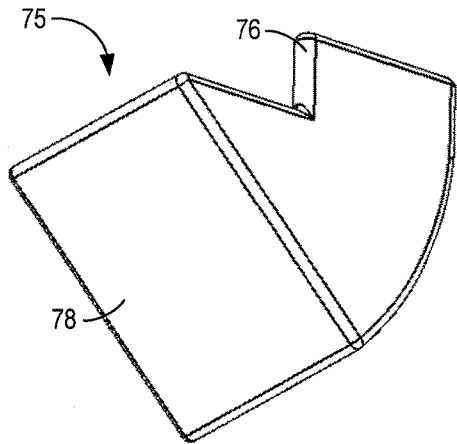
Figure 8C:
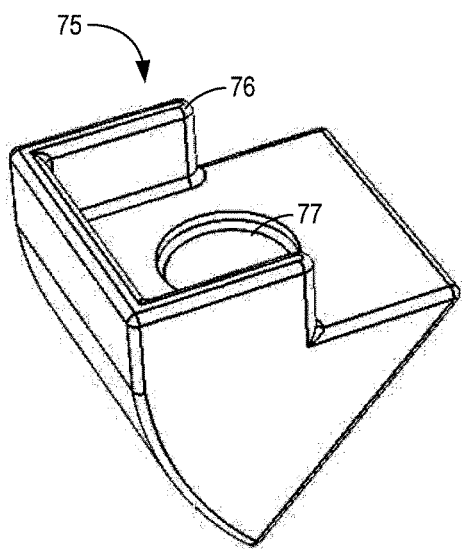
Figure 8D:
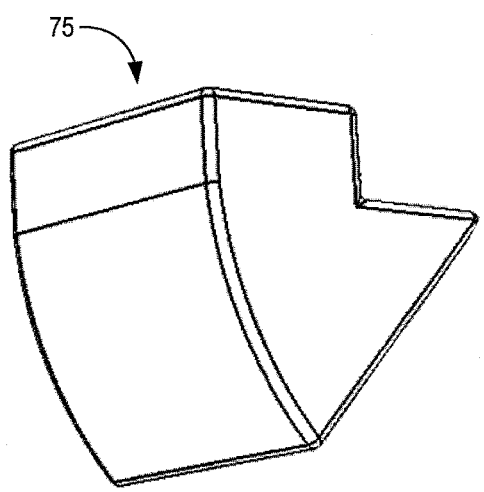

Referring to FIG. 7, for example, the bearing platform support members 80 comprise length-adjustable telescoping rods comprising an inner member 86 concentrically located within an outer member 84. The inner member 86 may be translated relative to outer member 84 to adjust the length of the bearing platform support members 80. The inner member 86 secured relative to outer member 84 with a locking screw 88, which sets the adjustable length of the bearing platform support members 80.

The bearing platform support members 80 may also comprise permanent magnets 82 located at opposite ends of each bearing platform support member 80. The bearing platform 20 may comprise at least two ferromagnetic attachment plates 28 located on the bottom side of the bearing platform 20. The base garment 70 may comprise at least two ferromagnetic attachment plates 72 located on shoulder surfaces of the base garment 70. The permanent magnets located at the opposite ends of each bearing platform support member 80 may engage and magnetically attach to the ferromagnetic attachment plates 28 located on the bottom side of the bearing platform 20, and to the ferromagnetic attachment plates 72 located on shoulder surfaces of the base garment 70. In this manner, as shown in FIG. 7, for example, the bearing platform support members 80 may be magnetically attachable to the base garment 70, and to the bottom side of the bearing platform 20. The ferromagnetic attachment plates 28/72 may be made of a ferromagnetic material of construction such as, for example, a stainless steel alloy.

Referring back to FIGS. 2C and 2D, the attachment plates 28 are shown located on the bottom sides of the holder bases 32 of the bearing platform 20. It is understood, however, that the attachment plates 28 can be located on any suitable portion of the bottom side of the bearing platform 20, such as, for example, on the bottom sides of the holder arms 34 (see FIGS. 11B, 11D, and 12, described in detail below).

The attachment plates 72 may be located on any suitable portion of the base garment 70; however, placement on the shoulder surfaces of the base garment 70 (i.e., the outer surfaces of the garment above a patient's shoulders may be most effective. The specific location of the attachment plates 72 on the shoulder surfaces of the base garment 70 may be dictated, at least in part, by the patient's specific anatomy. Accordingly, in some embodiments, a base garment may comprise adjustable base garment attachments instead of or in addition to attachment plates.

Although the embodiments, shown in FIGS. 6A, 6B, and 7 comprise magnets 82 connected to the bearing platform support members 80, and attachment plates 28/72 connected to the bearing platform 20 and the base garment 70, it is nevertheless understood that the relative orientation of these components may be switched, i.e., the bearing platform support members may have connected attachment plates, and the bearing platform and/or the base garment may have connected magnets.

FIGS. 8A-8D show an example of an adjustable base garment attachment 75. The adjustable base garment attachment 75 comprises a retaining wall 76, attachment plate 77, and engagement surface 78. The adjustable base garment attachment 75 is configured to be re-positionable on the surface of a base garment in order to provide the most effective releasable attachment position for bearing platform support members. For example, the adjustable base garment attachment 75 may comprise hook-and-loop closure (i.e., Velcro) materials connected to the engagement surface 78 and to the exterior surfaces of at least a portion (e.g., the shoulder surfaces) of a base garment (not shown). The mutual engagement of the hook-and-loop closure materials respectively connected to the engagement surface 78 and the base garment will secure the adjustable base garment attachment 75 to the base garment in a releasable and re-positionable manner at multiple locations on the exterior surfaces of the base garment. Alternatively, the adjustable base garment attachment 75 and a base garment may comprise a different releasable and re-positionable attachment mechanism such as, for example, snap fittings or magnetic fittings, respectively connected to the engagement surface 78 and to the exterior surfaces of at least a portion (e.g., the shoulder surfaces) of a base garment.

The attachment plate 77 of the adjustable base garment attachment 75 may be configured to releasably engage and attach to bearing platform support members (not shown). For example, the attachment plate 77 may comprise a ferromagnetic attachment plate that engages and magnetically attaches to permanent magnets located at an end of a bearing platform support member. The releasable and re-positionable (e.g., hook-and-loop, snap fitting, or magnetic) attachment capability of the adjustable base garment attachment 75 relative to a base garment, and the releasable (e.g., magnetic) attachment capability of the adjustable base garment attachment 75 to a bearing platform support member, may allow for the adjustable and customizable positioning of the cannula stabilization device on patient's of different size. The retaining wall 76 of the adjustable base garment attachment 75 may function to ensure that a bearing platform support member attached to the attachment plate 77 (e.g., magnetically attached) does not disengage from adjustable base garment attachment 75 during patient movement.

The bearing platform support members 80 are described as magnetically attachable to the base garment 70 and to the bearing platform 20 in connection with FIGS. 6B-8D. It is understood, however, that the attachment of the bearing platform support members 80 to the base garment 70 and to the bearing platform 20 is not limited to magnetic attachments, and alternatively can comprise, for example, releasable mechanical attachments such as snap fittings, fasteners (e.g., removable pins), hook-and-loop attachments (i.e., Velcro), and the like.

As described above, the helmet 60 is releasably attachable to the rotational joint 90 (for example, to the inner ring 92). As shown in FIGS. 5, 6A, and 6B, the releasable attachments may be implemented using, for example, fasteners 62 (e.g., screws, bolts, or the like) that are fixedly attached to the helmet 60 and positioned through the fastener holes 96 in the inner ring 92 of the rotational joint 90. In this manner, the helmet 60 and the rotational joint 90 may be fastened together, for example, with nuts and bolts. Alternatively, referring to FIG. 9, the helmet 60 and the rotational joint 90" may be magnetically (releasably) attached together with magnetic attachments 64. The magnetic attachments 64 may comprise a component 65 fixedly attached to the helmet 60, and a component 66 fixedly attached to the rotational joint 90". The helmet 60 may be releasably attached to the rotational joint 90" by engaging the two components 65 and 66 of the magnetic attachments 64. The helmet 60 may be de-attached from the rotational joint 90" by disengaging the two components 65 and 66 of the magnetic attachments 64.

Figure 10:
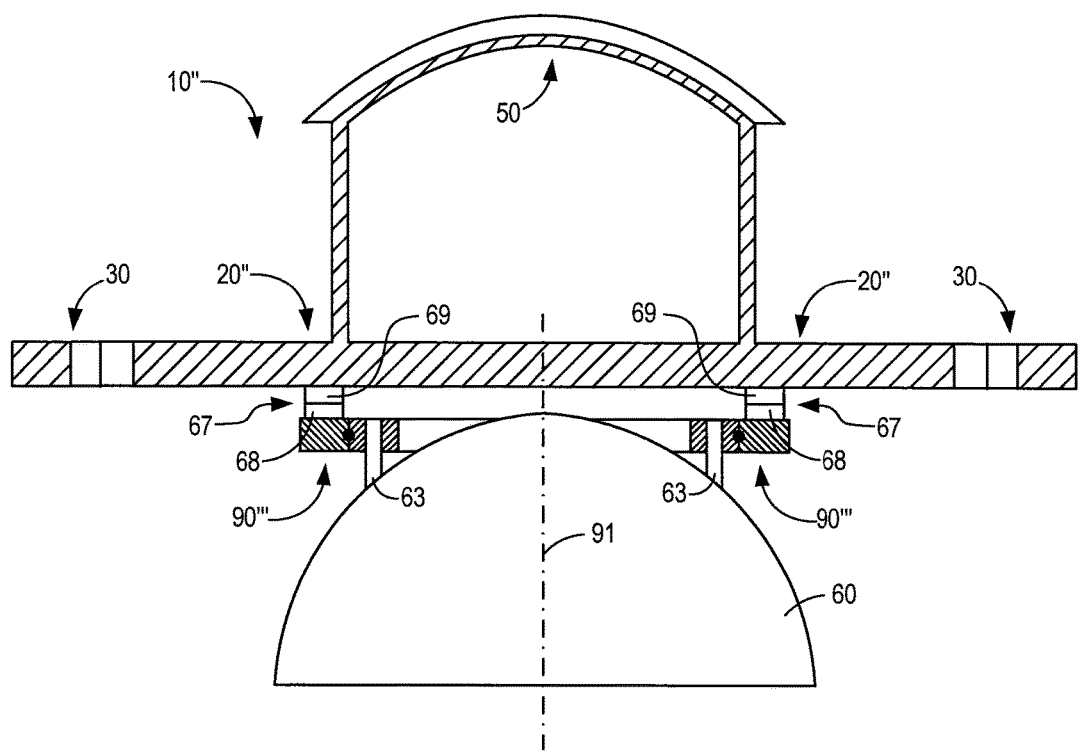
FIG. 10 is cross-sectional side view schematic diagram of a cannula stabilization device attached to a rotational joint with magnetic attachments and a patient helmet attached to the rotational joint with fasteners.

FIGS. 3C-6B and 9 show the rotational joint 90/90'/90" located in the countersunk pocket 26 in the bottom side of the bearing platform 20. However, it is understood that the rotation joint can be located in any suitable position that provides for the independent rotation of the helmet 60 and the bearing platform 20 around rotational axis 91. For example, referring to FIG. 10, the rotational joint 90''' can be fixedly attached to the helmet 60 using fastener 63. The rotational joint 90''' and the bearing platform 20" (and the tubing holders 30 and tubing track 50) may be magnetically (releasably) attached together with magnetic attachments 67. The magnetic attachments 67 may comprise a component 68 fixedly attached to the rotational joint 90''', and a component 69 fixedly attached to the bearing platform 20". The bearing platform 20" may be releasably attached to the rotational joint 90''' by engaging the two components 68 and 69 of the magnetic attachments 67. The bearing platform 20" may be de-attached from the rotational joint 90''' by disengaging the two components 68 and 69 of the magnetic attachments 67.

A prototype cannula stabilization device was made in accordance with the embodiments described in this specification. The prototype is shown in FIGS. 11A-11D and 12. As shown in FIGS. 11A-11D, the prototype cannula stabilization device comprises a bearing platform, a tubing holder located on a first end of the bearing platform, and a tubing holder located on a second end of the bearing platform opposite the first end. A tubing track is located on the top side of the bearing platform. The tubing track comprises two tubing track support members extending from the top side of the bearing platform and connecting to an arcuate shaped tubing support surface. The tubing track further comprises arcuate shaped tubing brackets located on opposite sides of the tubing support surface. A hook-and-loop closure (i.e., Velcro) strap is respectively connected to the end and side surfaces of the holder arms and the holder bases of each holder. Solid foam layers are located in the gaps in the holder arms and the holder bases of the tubing holders.

Figure 11B:
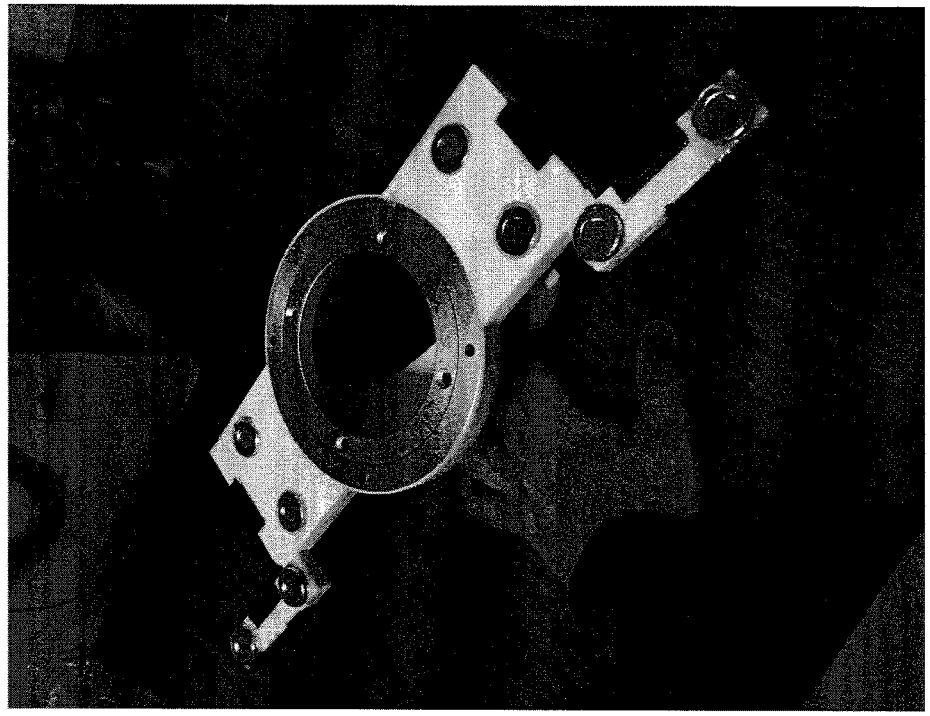
FIGS. 11A-11D are photographs showing a prototype cannula stabilization device comprising a bearing platform, rotational joint, tubing holders, and a tubing track.
Figure 11A:
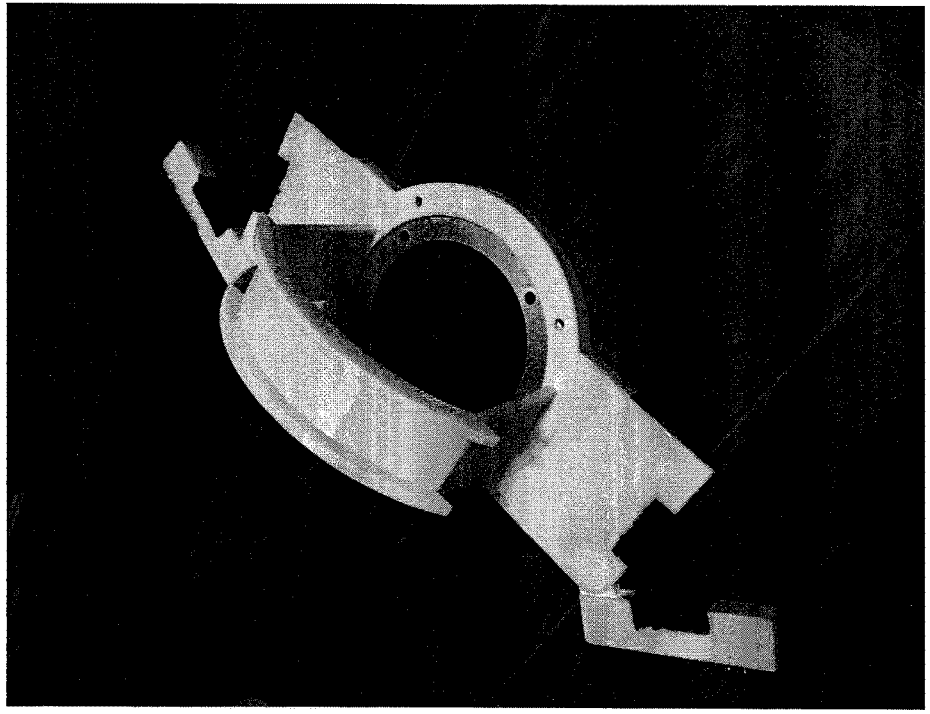
Figure 11D:
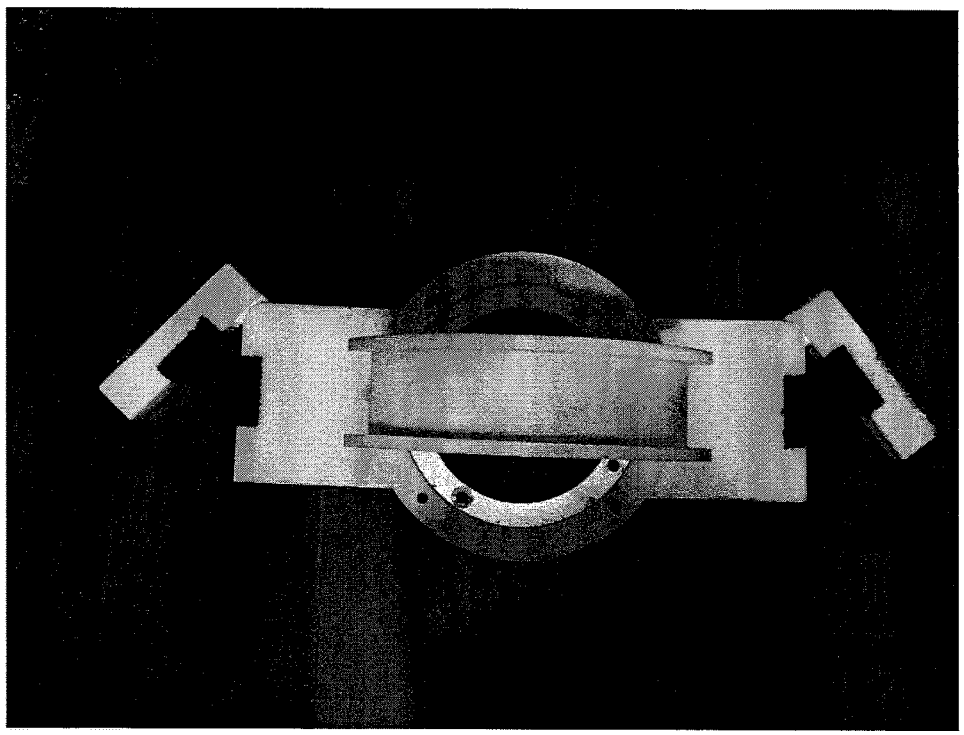
Figure 11C:
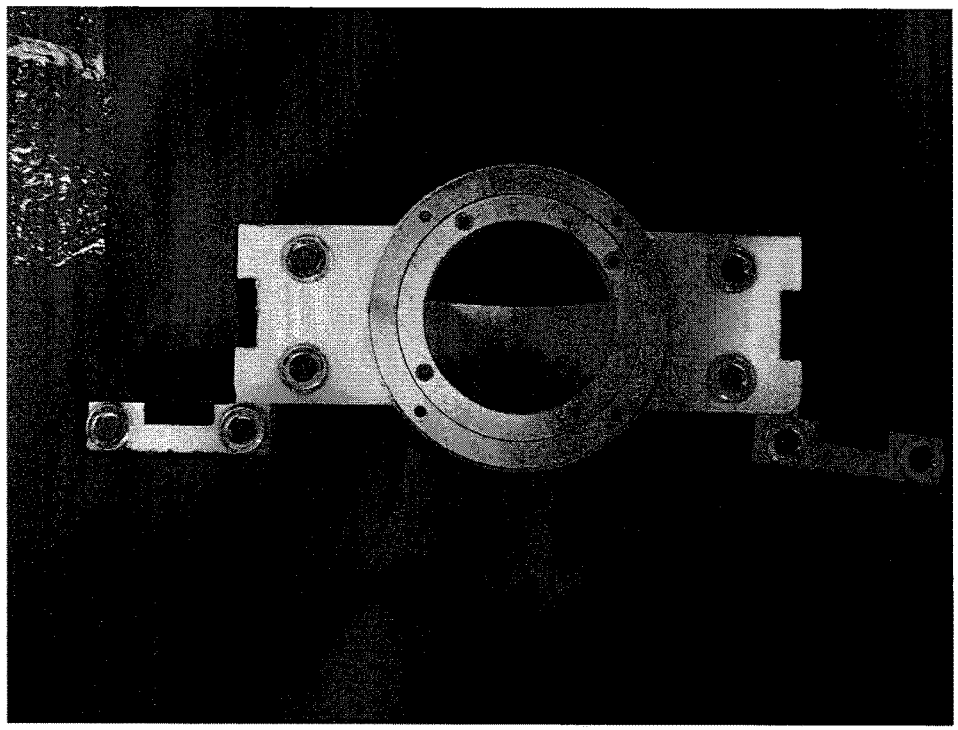

Still referring to FIGS. 11A-11D, the prototype cannula stabilization device comprises a rotational joint that is fixedly attached to the bearing platform in a countersunk pocket formed in the bottom side of the bearing platform. The rotational joint comprises an inner ring, an outer ring, and a plurality of ball bearings located between the inner ring and the outer ring. The inner ring and the outer ring are independently rotatable around a common rotational axis. The outer ring of the rotational joint is fixedly attached to the bearing platform. Referring specifically to FIGS. 11B and 11D, stainless steel attachment plates are located on the bottom sides of the holder bases of the bearing platform, and on the bottom sides of the holder arms.

Figure 12:
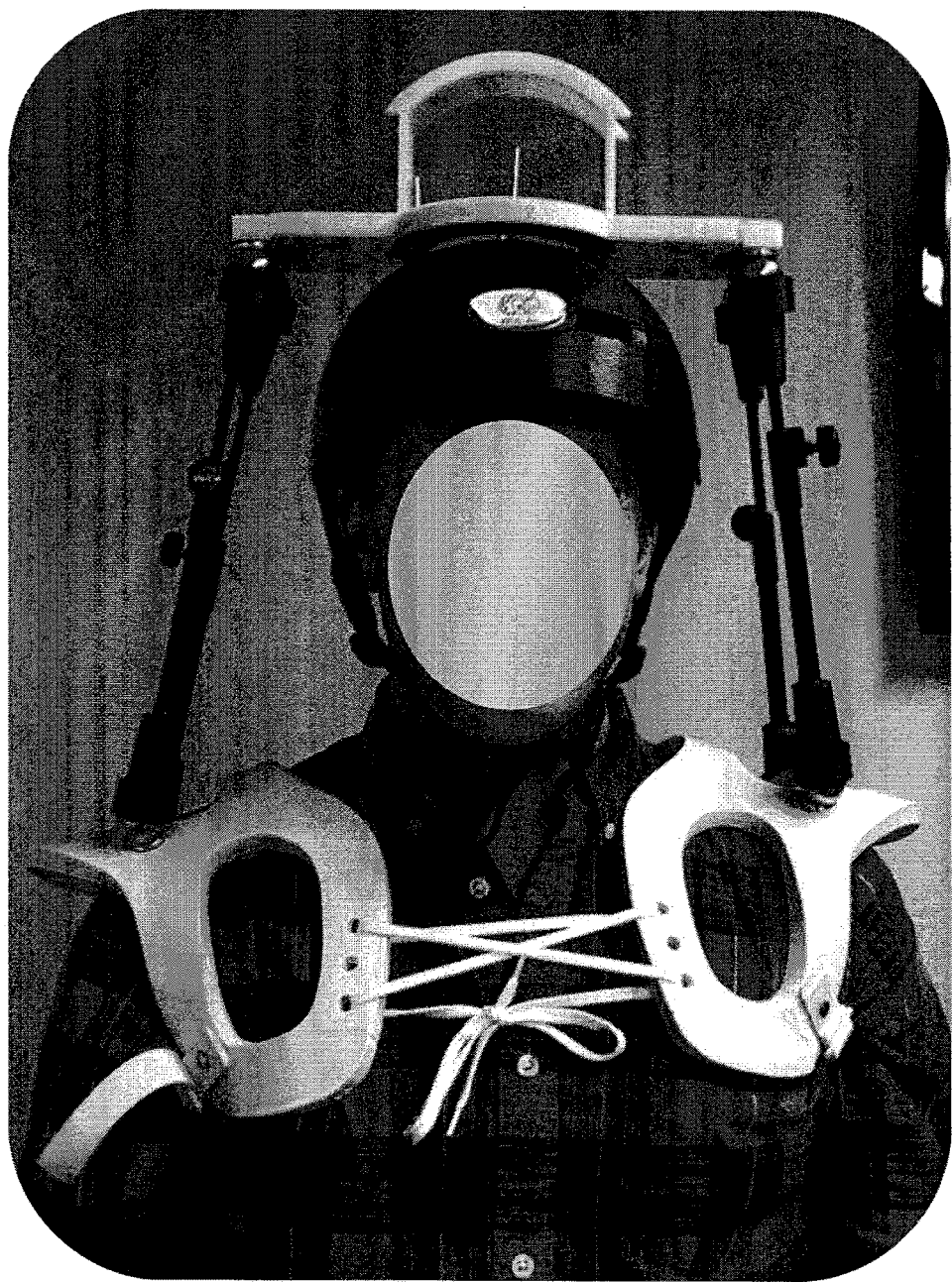
FIG. 12 is a photograph showing the prototype cannula stabilization device shown in FIGS. 11A-11D positioned on a human subject wearing a base garment and helmet; the rotational joint is fastened to the helmet and the bearing platform is magnetically attached to platform support members, which are magnetically attached to the base garment.

Referring to FIG. 12, the prototype cannula stabilization device is shown positioned on a human subject. The prototype cannula stabilization device further comprises a helmet that is releasably attachable to the inner ring of the rotational joint with nuts and bolts. The helmet (and therefore the human subject's head) is independently rotatable around a common rotational axis relative to bearing platform, tubing holders, and tubing track. The prototype cannula stabilization device further comprises a base garment in the form of adjustable shoulder pads and four bearing platform support members in the form of length-adjustable telescoping rods. Stainless steel attachment plates are located on the shoulder surfaces of the shoulder pads. As shown in FIG. 12, the bearing platform support members are magnetically (releasably) attached to the shoulder pads and to the bottom side of the bearing platform.

The prototype cannula stabilization device was used to verify and validate certain design criteria of the cannula stabilization devices described in this specification. A first design criterion was that use of the cannula stabilization device would stabilize a cannula insertion site so that the cannula could not move by more than 1 inch (2.45 cm) to minimize insertion site injury, potential for bleeding, and intravascular damage by cannula migration. This first design criterion was tested using a motion capture system on five human subjects. The subjects were fitted with motion capture tracking reflective dots and performed a set of motions, first without the cannula stabilization device and then with the cannula stabilization device. For all motions, a small piece of plastic was taped on each subject at the approximate location of a right jugular vein cannulation site on the subject's neck. This plastic piece was fitted with a reflective dot and tubing was placed through a hole in the piece to simulate tubing connected to a cannula. Two reflective dots were also placed on the tubing just above and just below the plastic piece. Using this set-up, it was determined that across all conditions (laying down to sitting up, sitting to standing, head rotations, walking, etc.) the tubing displaced an average of 0.35 cm±0.15 cm at the simulated cannula insertion site.

A second design criterion was that the cannula stabilization device would not disrupt blood flow through the tubing connecting a cannula to an external ECMO circuit. This design criterion was tested by creating a flow loop using a Biomedicus pump (Minneapolis, Minn.) and pressure transducers to measure the pressure drop across a short segment of tubing before and during placement into the cannula stabilization device. The pressure drop across the tubing both before and during placement into the cannula stabilization device was 1 mmHg. Therefore, the cannula stabilization device would not disrupt the blood flow through the tubing connecting a cannula to an external ECMO circuit.

The cannula stabilization device described in this specification simultaneously stabilizes the cannula insertion site, supports the tubing connected to the cannula, and maintains patient head mobility, which facilitates patient walking and ambulatory ECMO. While the cannula stabilization device has been described in this specification in connection with ECMO applications, it is nevertheless understood that the cannula stabilization device may be used in other central cannula applications where a cannula is inserted into a patient through a cannula insertion site in the patient's neck or upper torso, such as, for example, in the patient's armpit.

Figure 13A:
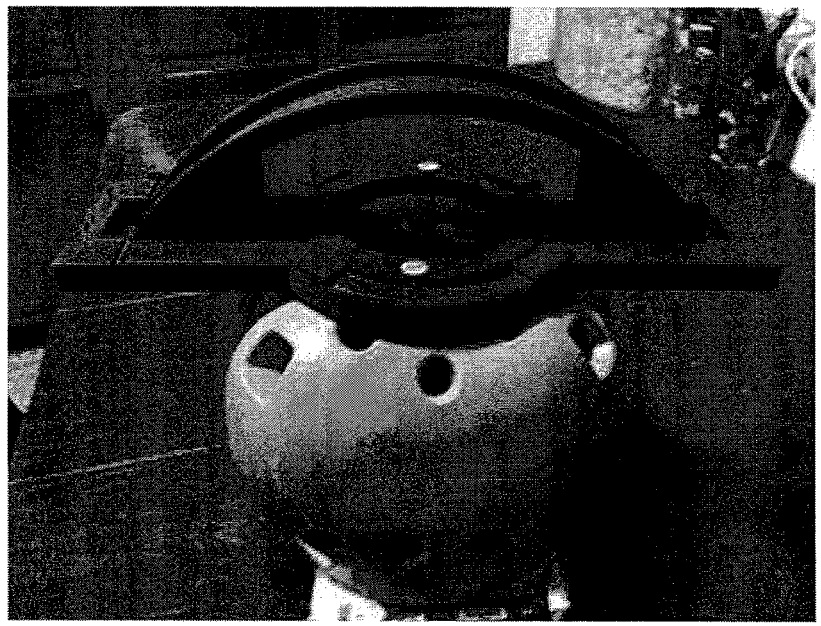
FIGS. 13A and 13B are photographs showing another prototype cannula stabilization device comprising a bearing platform, rotational joint, tubing holders, and a tubing track, wherein the prototype cannula stabilization device further comprises rotational stops configured to prevent over-rotation of a patient's head.
Figure 13B:
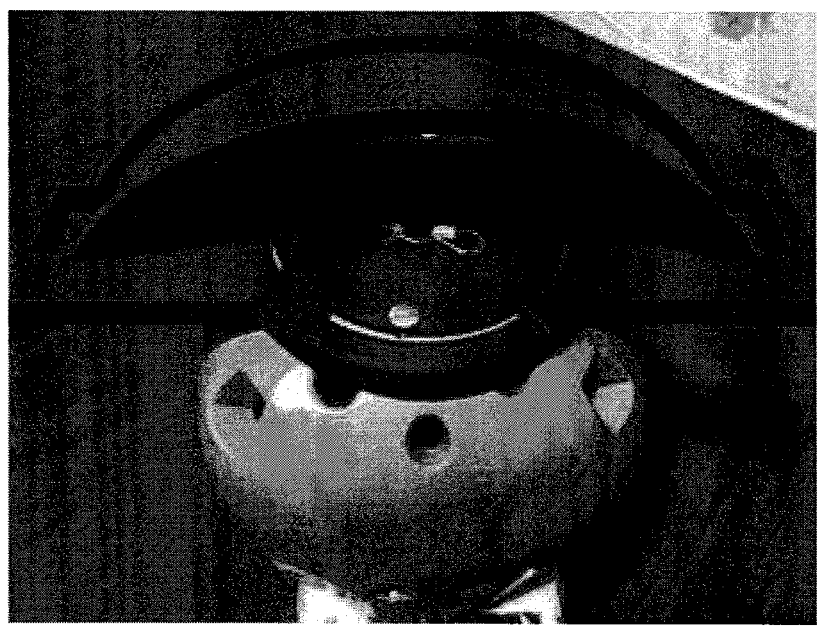

Another prototype cannula stabilization device was made in accordance with the embodiments described in this specification. The prototype is shown in FIGS. 13A and 13B. As shown in FIGS. 13A and 13B, the prototype cannula stabilization device comprises a bearing platform, a tubing holder located on a first end of the bearing platform, and a tubing holder located on a second end of the bearing platform opposite the first end. A tubing track is located on the top side of the bearing platform. The tubing track comprises two tubing track support brackets extending from the top side of the bearing platform and connecting to an arcuate shaped tubing support surface. The tubing support surface also extends from the top side of the bearing platform on opposed ends of the bearing platform, thus contacting the opposed ends of the holding bases and the opposed tubing apertures. The tubing track further comprises arcuate shaped tubing brackets located on opposite sides of the tubing support surface.

Still referring to FIGS. 13A and 13B, the prototype cannula stabilization device comprises a rotational joint that is fixedly attached to the bearing platform in a countersunk pocket formed in the bottom side of the bearing platform. The rotational joint comprises an inner ring, an outer ring, and a plurality of ball bearings located between the inner ring and the outer ring. The inner ring and the outer ring are independently rotatable around a common rotational axis. The outer ring of the rotational joint is fixedly attached to the bearing platform. The inner ring is attached to a bearing aperture cap that extends within the circumference of the inner ring, and the helmet is releasably attached to the inner ring through the bearing aperture cap using a pin fastener.

The bearing platform comprises rotational stops comprising integral projections extending from the top surface of the bearing platform. The inner ring of the rotational joint comprises rotational stops, which comprise integral projections extending from the top surface of the attached bearing aperture cap. The rotational stops of the inner ring/bearing aperture cap are located in an overlapping plane with the rotational stops of the bearing platform. Therefore, when a patient rotates their head and neck, as described above, the patient's rotational range is limited by the opposite positions at which the rotational stops of the inner ring/bearing aperture cap mechanically contact the rotational stops of the bearing platform.

Various features and characteristics of the inventions are described in this specification to provide an overall understanding of the disclosed cannula stabilization device. It is understood that the various features and characteristics described in this specification can be combined in any suitable manner regardless of whether such features and characteristics are expressly described in combination in this specification. The Applicants/Inventors expressly intend such combinations of features and characteristics to be included within the scope of this specification. As such, the claims can be amended to recite, in any combination, any features and characteristics expressly or inherently described in, or otherwise expressly or inherently supported by, this specification. Furthermore, the Applicants/Inventors reserve the right to amend the claims to affirmatively disclaim features and characteristics that may be present in the prior art, even if those features and characteristics are not expressly described in this specification. Therefore, any such amendments will comply with the written description requirement of 35 U.S.C. § 112(a), and will not add new matter to the specification or claims. The cannula stabilization device disclosed in this specification can comprise, consist of, or consist essentially of the various features and characteristics described in this specification.

Any patent, publication, or other disclosure material identified in this specification is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and can be employed or used in an implementation of the described processes, compositions, and products. Further, the use of a singular noun includes the plural, and the use of a plural noun includes the singular, unless the context of the usage requires otherwise.

REFERENCE CHARACTERS USED IN THE DRAWINGS

| Reference characters | Components/features |
| --- | --- |
| 1 | patient |
| 2 | patient's neck |
| 3 | cannula insertion site |
| 5 | ECMO circuit |
| 7 | cannula |
| 9 | tubing |
| 10 | cannula stabilization device |
| 20 | bearing platform |
| 22 | bearing base |
| 24 | bearing aperture |
| 26 | rotational joint pocket |
| 28 | attachment plates |
| 30 | tubing holder |
| 32 | holder base |
| 34 | holder arm |
| 36 | hinge |

-continued

| Reference characters | Components/features |
| --- | --- |
| 38 | tubing aperture |
| 42 | rotational stop |
| 44 | rotational stop |
| 50 | tubing track |
| 52 | tubing support surface |
| 54 | tubing brackets |
| 56 | tubing track support members |
| 60 | helmet |
| 62 | fasteners |
| 63 | fasteners |
| 64 | magnetic attachments |
| 65 | magnetic attachment component |
| 66 | magnetic attachment component |
| 67 | magnetic attachments |
| 68 | magnetic attachment component |
| 69 | magnetic attachment component |
| 70 | base garment |
| 72 | attachment plates |
| 75 | adjustable base garment attachments |
| 76 | retain wall |
| 77 | attachment plate |
| 78 | engagement surface |
| 80 | bearing platform support members |
| 82 | magnets |
| 84 | outer member |
| 86 | inner member |
| 88 | locking screw |
| 90 | rotational joint |
| 91 | rotational axis |
| 92 | inner ring |
| 94 | outer ring |
| 95 | ball bearing |
| 96 | fastener hole |
| 98 | rotational joint aperture |

What is claimed is:

1. A cannula stabilization device comprising:
   a bearing platform;
   a tubing holder located on a first end of the bearing platform;
   a tubing holder located on a second end of the bearing platform opposite the first end, wherein each tubing holder is configured to secure and route continuous tubing, and wherein the tubing is configured to intersect the bearing platform only at each tubing holder;
   a rotational joint fixedly attached to the bearing platform on a bottom side of the bearing platform; and
   a helmet releasably attachable to the rotational joint;
   wherein the helmet and the bearing platform are independently rotatable around a common rotational axis when the helmet is attached to the rotational joint.

2. The cannula stabilization device of claim 1, further comprising a tubing track located on a top side of the bearing platform.

3. The cannula stabilization device of claim 2, wherein the tubing track comprises at least two tubing track support members extending from the top side of the bearing platform and connecting to a tubing support surface.

4. The cannula stabilization device of claim 3, wherein the tubing support surface is arcuate shaped and the tubing track further comprises arcuate shaped tubing brackets located on opposite sides of the tubing support surface.

5. The cannula stabilization device of claim 1, further comprising:
   a base garment configured to be worn by a cannulated patient; and
   at least two bearing platform support members;
   wherein the bearing platform support members are releasably attachable to the base garment, and wherein the bearing platform support members are releasably attachable to the bottom side of the bearing platform.

6. The cannula stabilization device of claim 5, wherein the bearing platform support members comprise length-adjustable telescoping rods.

7. The cannula stabilization device of claim 5, wherein the releasable attachments between the bearing platform support members and the base garment and/or the bottom side of the bearing platform comprise magnetic attachments, snap fittings, pins, or hook-and-loop attachments.

8. The cannula stabilization device of claim 7, wherein:
the bearing platform comprises at least two ferromagnetic attachment plates located on the bottom side of the bearing platform;
the base garment comprises at least two ferromagnetic attachment plates located on shoulder surfaces of the garment; and
the bearing platform support members each comprise permanent magnets located at opposite ends of each bearing platform support member.

9. The cannula stabilization device of claim 1, wherein the tubing holders each comprise a holder arm attached to a holder base through a hinge.

10. The cannula stabilization device of claim 9, wherein the holder arm and the holder base each comprise gaps that together form a tubing aperture through the tubing holder in a closed configuration.

11. The cannula stabilization device of claim 10, wherein the holder arm and/or the holder base of each tubing holder further comprises foam located in the gap.

12. The cannula stabilization device of claim 1, wherein:
the rotational joint comprises an inner ring, an outer ring, and a plurality of ball bearings located between the inner ring and the outer ring;
the inner ring and the outer ring are independently rotatable around the common rotational axis;
the outer ring of the rotational joint is fixedly attached to the bearing platform on the bottom side of the bearing platform; and
the helmet is releasably attachable to the inner ring of the rotational joint.

13. The cannula stabilization device of claim 1, wherein the rotational joint is fixedly attached to the bearing platform in a countersunk pocket formed in the bottom side of the bearing platform.

14. The cannula stabilization device of claim 1, wherein the bearing platform comprises a bearing aperture extending from the top side of the bearing platform to the bottom side of the bearing platform, and wherein the rotational joint is located in concentric alignment with the bearing aperture.

15. The cannula stabilization device of claim 14, wherein the rotational joint is fixedly attached to the bearing platform in a countersunk pocket formed in the bottom side of the bearing platform, and wherein the countersunk pocket is located in concentric alignment with the bearing aperture.

16. The cannula stabilization device of claim 1, wherein the helmet is releasably attachable to the rotational joint with fasteners or magnetic attachments.

17. The cannula stabilization device of claim 16, wherein the helmet is magnetically attachable to the rotational joint with a pin fastener.

18. A cannula stabilization device comprising:
a bearing platform;
a tubing holder located on a first end of the bearing platform;
a tubing holder located on a second end of the bearing platform opposite the first end;
a tubing track located on a top side of the bearing platform, the tubing track comprising at least two tubing track support members or brackets extending from the top side of the bearing platform and connecting to an arcuate shaped tubing support surface, and further comprising arcuate shaped tubing brackets located on opposite sides of the tubing support surface;
a rotational joint fixedly attached to the bearing platform in a countersunk pocket formed in a bottom side of the bearing platform, wherein the rotational joint comprises an inner ring, an outer ring, and a plurality of ball bearings located between the inner ring and the outer ring, wherein the inner ring and the outer ring are independently rotatable around a common rotational axis, and wherein the outer ring of the rotational joint is fixedly attached to the bearing platform; and
a helmet releasably attachable to the inner ring of the rotational joint, wherein the helmet and the bearing platform are independently rotatable around the common rotational axis when the helmet is attached to the rotational joint.

19. The cannula stabilization device of claim 18, further comprising:
a base garment configured to be worn by a cannulated patient; and
at least two bearing platform support members comprising length-adjustable telescoping rods;
wherein the bearing platform support members are magnetically attachable to the bottom side of the bearing platform.

20. The cannula stabilization device of claim 18, wherein the helmet is releasably attachable to the rotational joint with fasteners or magnetic attachments.

* * * * *